US012096921B2

(12) United States Patent
Goldenberg et al.

(10) Patent No.: US 12,096,921 B2
(45) Date of Patent: Sep. 24, 2024

(54) BIOPSY NEEDLE

(71) Applicant: FullCore, LLC, Atlanta, GA (US)

(72) Inventors: Alec Goldenberg, New York, NY (US); Matt Pursley, Dawsonville, GA (US); Paul Hendrixson, Cumming, GA (US); Paul Gianneschi, Atlanta, GA (US)

(73) Assignee: FullCore, LLC, Atlanta, GA (US)

( * ) Notice: Subject to any disclaimer, the term of this patent is extended or adjusted under 35 U.S.C. 154(b) by 0 days.

(21) Appl. No.: 18/110,109

(22) Filed: Feb. 15, 2023

(65) Prior Publication Data

US 2023/0190247 A1 Jun. 22, 2023

Related U.S. Application Data

(62) Division of application No. 15/947,544, filed on Apr. 6, 2018, now Pat. No. 11,612,383.

(60) Provisional application No. 62/482,344, filed on Apr. 6, 2017.

(51) Int. Cl.
*A61B 10/02* (2006.01)
*A61B 10/04* (2006.01)
*A61B 17/00* (2006.01)
A61B 17/32 (2006.01)
A61B 17/34 (2006.01)

(52) U.S. Cl.
CPC ......... *A61B 10/0275* (2013.01); *A61B 10/04* (2013.01); *A61B 17/00234* (2013.01); *A61B 2010/0208* (2013.01); *A61B 2017/320064* (2013.01); *A61B 17/3403* (2013.01)

(58) Field of Classification Search
CPC ............... A61B 10/0275; A61B 10/04; A61B 17/00234; A61B 17/3403
See application file for complete search history.

(56) References Cited

U.S. PATENT DOCUMENTS

| 3,605,721 A | 9/1971 | Hallac |
| 4,699,154 A | 10/1987 | Lindgren |
| 4,958,625 A | 9/1990 | Bates et al. |
| 5,400,798 A | 3/1995 | Baran |
| 5,415,182 A | 5/1995 | Chin |
| 5,505,211 A | 4/1996 | Ohto |
| 5,522,398 A | 6/1996 | Goldenberg et al. |
| 5,843,001 A | 12/1998 | Goldenberg |

(Continued)

FOREIGN PATENT DOCUMENTS

| EP | 0 238 461 | 9/1987 |
| GB | 747617 | 4/1956 |
| WO | WO 2016/158060 | 10/2016 |

*Primary Examiner* — Daniel L Cerioni
(74) *Attorney, Agent, or Firm* — Leason Ellis LLP

(57) ABSTRACT

A biopsy needle for collecting a tissue specimen includes an outer cannula and an inner tube received within the outer cannula. A snare coil is attached between the inner tube and the outer cannula and is configured to wind down when the inner tube rotates in a first direction relative to the outer cannula. The outer cannula is fixedly coupled to a needle holder that is coupled to and moves with a movable base that is axially movable within the handle housing. An inner driven structure (curvilinear part) is configured to selectively engage the movable base and travel therewith in a first stage of operation and in a second stage of operation in which the inner driven structure is disengaged from the movable base, the inner driven structure is driven along the movable base which is held in a stationary position.

25 Claims, 28 Drawing Sheets

(56) References Cited

U.S. PATENT DOCUMENTS

| | | |
|---|---|---|
| 5,865,826 A | 2/1999 | Volker |
| 6,015,391 A | 1/2000 | Rishton et al. |
| 6,033,369 A | 3/2000 | Goldenberg |
| 6,120,463 A | 9/2000 | Bauer |
| 6,340,351 B1 | 1/2002 | Goldenberg |
| 7,207,950 B2 | 4/2007 | Goldenberg |
| 7,226,423 B2 | 6/2007 | Goldenberg |
| 7,278,970 B2 | 10/2007 | Goldenberg |
| 7,338,456 B2 | 3/2008 | Goldenberg |
| 7,384,400 B2 | 6/2008 | Goldenberg |
| 7,455,645 B2 | 11/2008 | Goldenberg |
| 7,608,048 B2 | 10/2009 | Goldenberg |
| 7,608,049 B2 | 10/2009 | Goldenberg |
| 7,621,923 B2 | 11/2009 | Goldenberg |
| 7,700,046 B2 | 4/2010 | Goldenberg |
| 7,731,667 B2 | 6/2010 | Goldenberg |
| 7,862,518 B2 | 1/2011 | Parihar |
| 8,052,616 B2 | 11/2011 | Andrisek et al. |
| 8,398,566 B2 | 3/2013 | Goldenberg |
| 8,500,654 B2 | 8/2013 | Goldenberg |
| 8,894,586 B2 | 11/2014 | Goldenberg |
| 9,211,113 B2 | 12/2015 | Goldenberg |
| 2005/0054947 A1 | 3/2005 | Goldenberg |
| 2005/0054948 A1 | 3/2005 | Goldenberg |
| 2007/0219460 A1 | 9/2007 | Goldenberg |
| 2008/0281223 A1 | 11/2008 | Goldenberg |
| 2008/0281226 A1 | 11/2008 | Peters |
| 2009/0118641 A1 | 5/2009 | Van Dam et al. |
| 2009/0204023 A1 | 8/2009 | Goldenberg |
| 2009/0227895 A1 | 9/2009 | Goldenberg |
| 2010/0160814 A1 | 6/2010 | Parihar |
| 2010/0160823 A1 | 6/2010 | Parihar |
| 2011/0004120 A1 | 1/2011 | Drubetsky |
| 2012/0150066 A1 | 6/2012 | Goldenberg |
| 2012/0265094 A1 | 10/2012 | Goldfarb et al. |
| 2015/0073299 A1 | 3/2015 | Vetter |
| 2015/0238171 A1 | 8/2015 | Shabaz |
| 2016/0135793 A1 | 5/2016 | Goldenberg |
| 2016/0135794 A1 | 5/2016 | Goldenberg |
| 2017/0135693 A1 | 5/2017 | Cardinale |

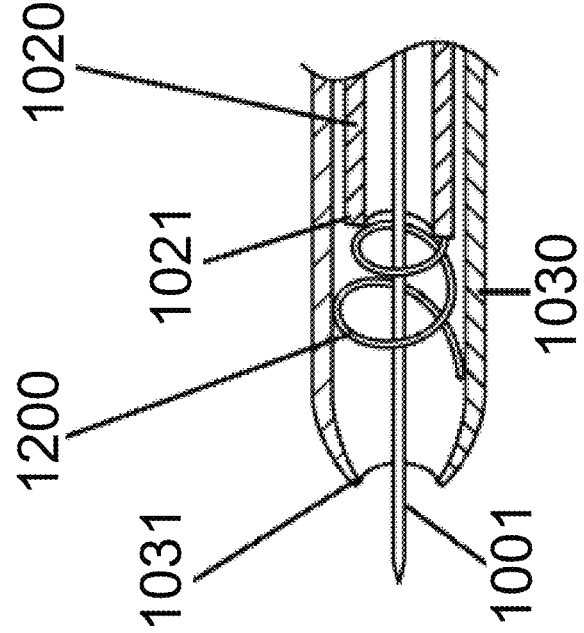

BIOPSY NEEDLE

CROSS-REFERENCE TO RELATED APPLICATIONS

This patent application is a divisional of U.S. patent application Ser. No. 15/947,544, filed Apr. 6, 2018, which is based on and claims priority to U.S. Provisional Patent Application 62/482,344, filed Apr. 6, 2017 and is related to U.S. patent application Ser. No. 14/939,805, filed Nov. 12, 2015, which is claims priority to U.S. Patent Application Ser. No. 62/081,257, filed Nov. 18, 2014 and U.S. Patent Application Ser. No. 62/170,934, filed Jun. 4, 2015, each of which is hereby respectively incorporated by reference as if set forth in its respective entirety herein.

TECHNICAL FIELD

The present invention relates to a surgical instrument, typically known as a biopsy device used to obtain tissue samples of a target specimen and more particularly, relates to a minimally invasive biopsy device that allows an operator to more precisely obtain substantially larger tissue samples by manipulating the device's cutting mechanism for efficient engagement with a lesion or mass, resulting in improved sampling of organs or other anatomical structures.

BACKGROUND

Patients are undergoing more minimally invasive procedures as alternatives to open surgical procedures. These less invasive biopsy procedures use a variety of devices which are placed in organs and tissues, or abdominal, pulmonary, urologic spaces with the goal of sampling tissues, masses, or lymph nodes to establish a histopathologic diagnosis.

Standard or direct explorations or excisions of tissue samples, can be overly invasive and traumatic, and inconsistent with the basic principles of minimizing direct trauma through minimally invasive procedures. Therefore, minimally invasive devices and techniques have been developed to retrieve samples of suspicious lesions, or masses.

There are a number of shortcomings in the designs of conventional biopsy devices and their application in clinical practice which limits their effectiveness and/or simplicity. The success of the biopsy procedure depends on the ability of the sampling device to efficiently and reliably obtain a tissue sample. The initial steps of a biopsy procedure require that the sampling device must come in contact with the target tissue in a way that allows the device to engage it.

The object of the present invention is to provide a device that overcomes these deficiencies and improves the biopsy procedure.

Other features and advantages of the present invention will be apparent from the following detailed description when read in conjunction with the accompanying drawings.

SUMMARY

A biopsy needle for collecting a tissue specimen includes an outer cannula that is at least partially received within a handle housing and an inner tube received within the outer cannula and configured to receive a stylet. A snare coil is attached between the inner tube and the outer cannula and is configured to wind down when the inner tube rotates in a first direction relative to the outer cannula and uncoil when the inner tube rotates in a second direction relative to the outer cannula. The outer cannula is fixedly coupled to a needle holder that is coupled to and moves with a movable base that is axially movable within the handle housing. An inner driven structure (curvilinear part) is configured to selectively engage the movable base and travel therewith in a first stage of operation and in a second stage of operation in which the inner driven structure is disengaged from the movable base, the inner driven structure is driven along the movable base which is held in a stationary position. The coupling between the inner driven structure and the inner tube is such that the axial driving of the inner driven structure imparts rotation to the inner tube relative to the outer cannula.

The needle includes a biasing mechanism that imparts a force on the inner driven structure for driving the inner driven structure in a distal direction when the biasing mechanism releases its stored energy. Since in the first stage of operation, the inner driven structure engages the movable base, the movable base is likewise driven in the distal direction along its permitted path of travel. Once the movable base reaches the end of the permitted path of travel, the second stage of operation initiates and the inner driven structure disengages from the movable base and is driven distally by the force applied by the biasing mechanism.

As described herein, the movable base is constructed so that disengagement of the inner driven structure from the movable base automatically occurs when the movable base reaches its end of permitted travel and the movable base is prevented from moving proximally when the inner tube rotates relative to the outer cannula.

The device also includes a reset mechanism that is designed to move both the inner driven structure and the movable base back to their initial fully cocked positions in which the biasing mechanism is compressed and stores energy. An actuator is provided for releasing the combined movable base and inner driven structure and this results in the release of the stored energy and the driving of the combined movable base and inner driven structure in the distal direction. As described herein, the rest mechanism can be defined by two separate cocking operations, namely a first cocking action and a second cocking action.

DETAILED DESCRIPTION OF THE DRAWING FIGURES

FIG. 47 is a partial cross-sectional view of a distal end of the needle assembly.

DETAILED DESCRIPTION OF CERTAIN EMBODIMENTS

Figure 1:
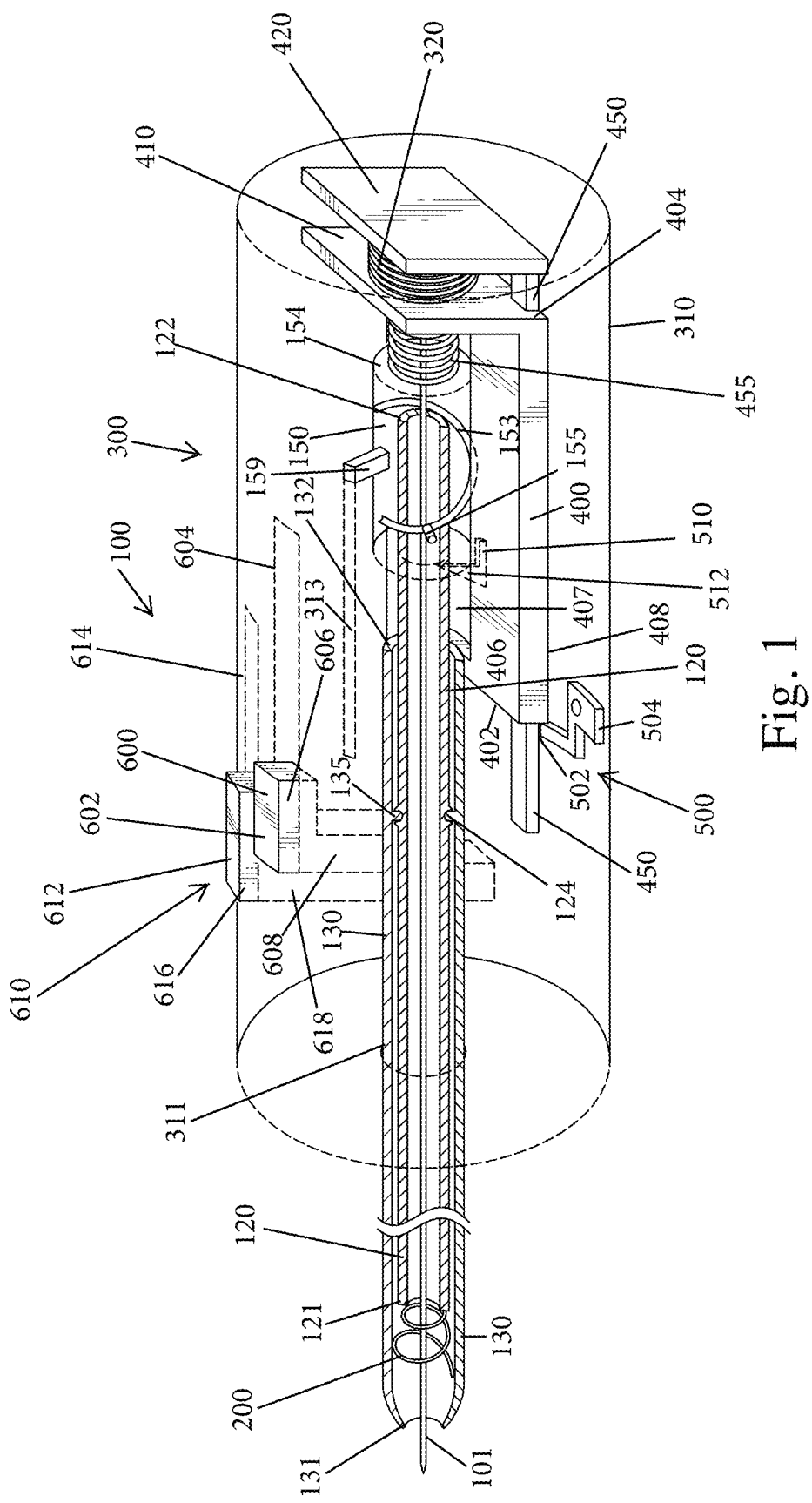
FIG. 1 is a side perspective view of a biopsy device in an initial position prior to actuation.
Figure 2:
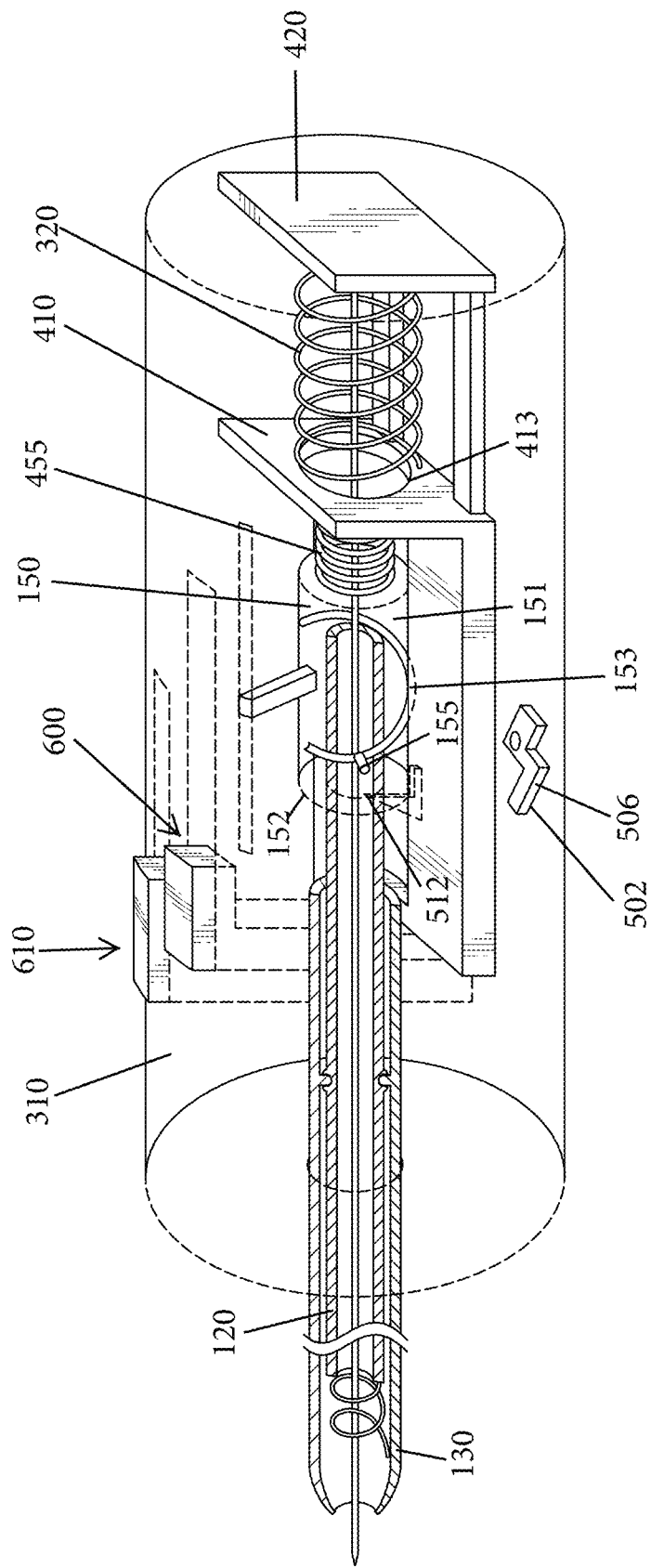
FIG. 2 is a side perspective view of the biopsy device after completion of a first stage of operation.
Figure 3:
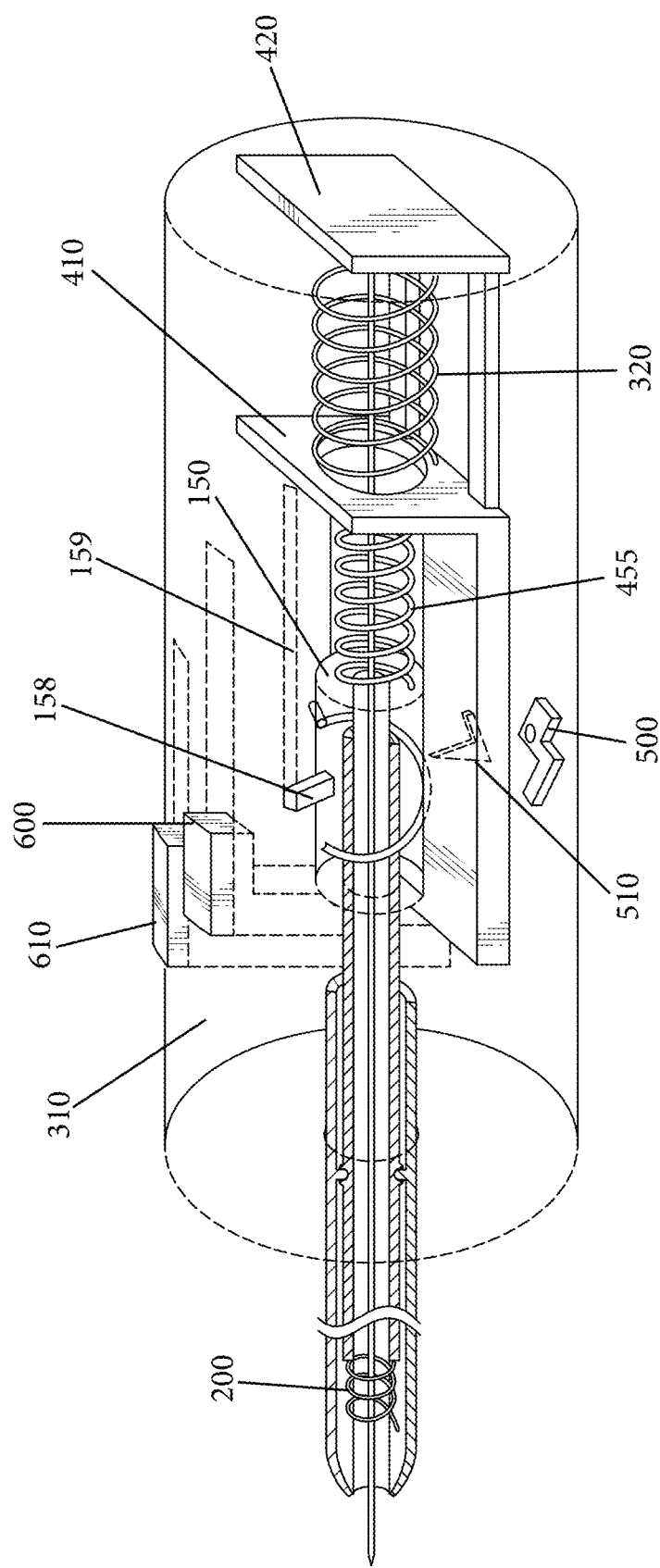
FIG. 3 is a side perspective view of the biopsy device after completion of a second stage of operation.

Now referring to FIGS. 1-3 in which a biopsy device 100 (specimen retrieving and capturing device or biopsy needle) of a snare coil design is illustrated and is configured to retrieve a target specimen which can be in the form of a tissue specimen or a foreign material that is located in certain organs or anatomical structures. To facilitate entry of the biopsy/capturing device 100 into organs or anatomical structures or duct channels, the device 100 incorporates a catheter system.

Referring now to FIGS. 1-3, the retrieval device (biopsy needle) 100 according to one exemplary embodiment is illustrated. The biopsy needle 100 includes an inner tube 120 with a (snare coil) wire 200 at a distal end thereof, an outer cannula 130, a stylet 101 and a handle assembly 300. In one aspect of the present invention, the handle assembly 300 includes a biasing (spring loaded) mechanism described in greater detail below that permits the user to selectively actuate the biopsy needle 100 so that the outer cannula 130 and the inner tube 120 are rapidly advanced beyond the stylet 101 to provide a shearing action of the soft tissue specimen.

The present biopsy needle 100 is particularly constructed for soft tissue biopsy applications since the spring loaded mechanism provides an improved means of removing the tissue after it is cored as well as providing an improvement in the way that the tissue is acquired by the biopsy needle 100. The handle assembly 300 includes a handle body 310 that can be formed in a number of different shapes and sizes and is generally a hollow body that contains the spring loaded mechanism. For purpose of illustration only, the handle body 310 of FIG. 1 is a generally rectangular or cylindrical or square body; however, handle body 310 preferably is an ergonomically pleasing shape that allows for secure grasping and accurate positioning of the needle tip by the operator.

The inner tube 120 includes a distal end 121 and an opposing proximal end 122. The inner tube 120 can have any number of different cross-sectional shapes; however, in one embodiment, the inner tube 120 has a circular cross-section. The inner tube 120 can include an annular shaped groove 124 that is spaced from the proximal end 122.

The outer cannula 130 can be similar or identical to the outer tube disclosed in one of the aforementioned patents. More specifically, the outer cannula 130 can include a distal end 131 and an opposing proximal end 132. The outer cannula 130 can also have any number of different cross-sectional shapes with one embodiment being a circular tube structure. At or near the proximal end of the outer cannula 130, the outer cannula 130 can include a protrusion 135, such as a bump, that mates with and is received within the annular groove 124. A snap-fit can be formed between the outer cannula 130 and the inner tube 120. The reception of the protrusion 135 into the annular groove 124 couples the two members together such that the two members move longitudinally in unison, while the inner tube 120 can rotate relative to the outer cannula 130 (i.e., the bump travels within the annular groove).

In accordance with the present invention, the inner tube 120 and the outer cannula 130 are coupled to one another such that the inner tube 120 and the outer cannula 130 move together, in unison, in an axial direction, while the inner tube 120 is permitted to rotate relative to the outer cannula 130 for activating and deactivating the snare. Any number of different mechanisms can be used to achieve the foregoing coupling between the outer cannula 130 and the inner tube 120.

Figure 1A:
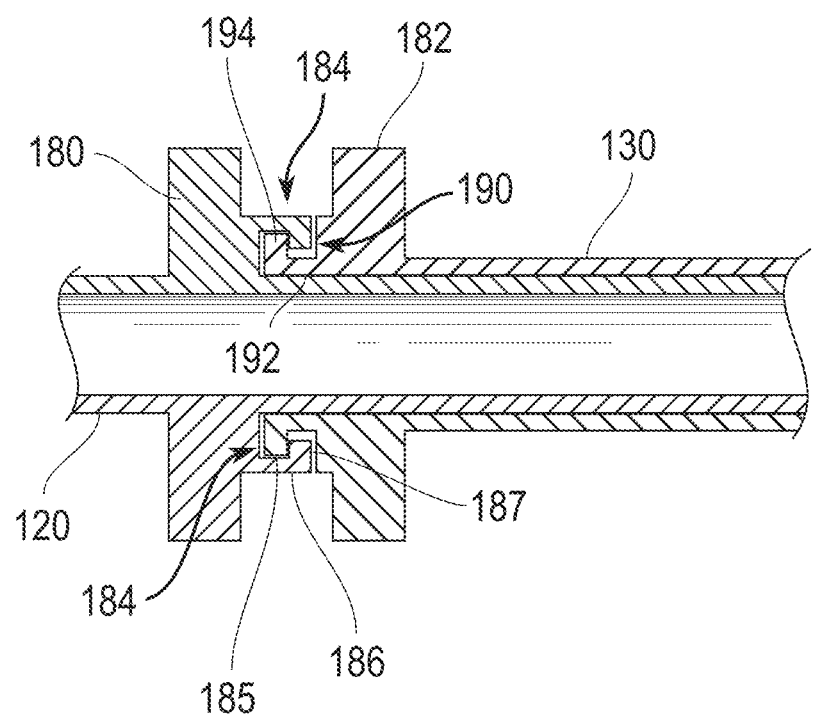
FIG. 1A is a cross-sectional view of an alternative mechanism for coupling an inner tube and outer cannula of the device.

Alternatively and as shown in FIG. 1A, the inner tube 120 can include a flange 180 that is spaced from the proximal end 122 and extends outwardly from the inner tube 120. The flange 180 can be in the form of an annular flange that extends completely around the inner tube 120 or it can be in the form of one or more protrusions, e.g., tabs, that extend outward from the inner tube 120. The flange 180 can be in the form of an annular ring.

Alternatively, at the proximal end 132 of the outer cannula 130, a flange 182 is formed. As with the flange 180 formed as part of the inner tube 120, the flange 182 of the outer cannula 130 can be in the form of an annular flange or it can be formed by one or more protrusions or tabs.

The inner tube flange 180 and the outer tube flange 182 can be positioned adjacent to each other along the longitudinal axis of the inner tube/outer tube assembly to limit displacement of the tubes relative to each other when they are both projected forward or repositioned back into the handle assembly. Alternatively, the inner tube flange 180 may be positioned adjacent to the proximal end of the outer tube 130 to limit displacement of the inner and outer tubes 120, 130 relative to each other during forward projection of the inner/outer tube or repositioning of the inner/outer tube into the handle assembly. In this side by side flange configuration, the inner and outer tubes 120, 130 remain aligned and move uniformly without displacing the one tube relative to the other tube, partly as a result of the lip and groove engagement mechanism represented by the annular groove 124 and the protrusion 135.

In one embodiment, shown in FIG. 1A, in which the inner tube 120 and outer cannula 130 include flanges 180, 182, respectively, the flange 180 of the inner tube 120 includes a first locking lip 184 that creates a space 185 between the lip 184 and the flange 180. The first locking lip 184 has a first portion 186 and a second portion 187 that is parallel to the flange 180, with the first portion 186 being perpendicular to the flange 180 and connects the second portion 187 to the flange 180.

The outer cannula 130 includes a complementary second locking lip 190 that is received within space 185 between the first locking lip 184 and the flange 180, thereby coupling the parts 120, 130 to one another. The second locking lip 190 has a first portion 192 and a second portion 194 that is parallel to the flange 182, with the first portion 192 being perpendicular to the flange 182 and connects the second portion 194 to the flange 182. The second portion 194 is parallel to flange 182. The second portion 194 is thus received within the space 185, thereby coupling the two 120, 130 together in a longitudinal direction, while permitting the two 120, 130 to rotate relative to one another. In this manner, the lip portions interlock with one another and prevent independent axial movement between the inner tube 120 and the outer cannula 130, while still permitting rotation of the inner tube 120 relative to the outer cannula 130.

In the case of the protrusion 135 and annular groove 124 embodiment, as illustrated, the protrusion 135 is received in the groove 124 and releasably retained therein.

The handle body 310 includes an opening 311 formed at a distal end thereof through which the combined inner tube 120/outer cannula 130 pass. The opening 311 allows the combined inner tube 120/outer cannula 130 to move in the axial direction between the retracted position and the extended position in which more of the combined inner tube 120/outer cannula 130 is exposed distally beyond and outside of the handle body 310. This opening 311 allows the combined inner tube/outer cannula to be fired and retracted as described herein.

Both the inner tube 120 and the outer cannula 130 are axially movable through the displacement of a movable base 400 that is disposed within the handle body 310. The movable base 400 can be thought of as being a sled that is controllably moved a defined distance within the hollow interior of the housing 300. The base 400 has a first end 402, an opposing second end 404, a top surface 406 and an opposing bottom surface 408. In accordance with the present invention, the combined inner tube 120/outer cannula 130 are coupled to the base 400 such that the axial movement of the base 400 (in either direction) is translated into axial movement of the combined inner tube 120/outer cannula 130. More specifically, the outer cannula 130 can be coupled to the top surface 406 of the base 400 using any suitable technique. For example, a mechanical coupling (fit) can be formed or an adhesive or chemical bonding can be used.

In one embodiment, the combined inner tube 120/outer cannula 130 is fixedly attached to the base 400 such that the base 400 acts as a carrier for the combined inner tube 120/outer cannula 130.

In one embodiment, the top surface 406 has a contoured surface in which the top surface 406 includes a recessed section and more specifically, the recessed section in the top surface 406 comprises a concave section 407 defined by a concave surface. The concave surface 407 does not have to extend the entire length of the top surface 406 but instead can only extend a length thereof less than the entire length. When the concave surface 407 does not extend to either of the ends of the base 400, the concave surface 407 can be defined by a first end edge and/or a second end edge. As described below, one or more of these end edges can act as a stop. Alternatively, the top surface recessed section may be configured in other non-concave morphologic conformations.

There are any number of different ways to construct the base 400 such that it is axially movable within the handle body 310. In particular, the base 400 can ride along one or more guides 450 that permit axial movement both in a distal direction and a proximal direction. For example, a pair of guides 450 can be provided with each of the guides 450 being in the form of an elongated rod. The two rods 450 are fixedly anchored at their ends to the ends of the handle body 310. The two rods 450 are thus spaced apart from one another and are parallel to one another. The base 400 has a pair of bores formed along a length thereof and configured to receive the rods 450. The base 400 thus freely rides along the rods 450 in both a distal axial direction and a proximal axial direction. The rods 450 also support and suspend the base 400 within the hollow interior of the handle body 310.

Alternatively, the base 400 can have one or more tabs or fingers that depress downwardly therefrom and are received within a complementary received track formed in the handle body 310. The recessed track is a longitudinal track that allows the base 400 to move in an axial direction within the handle body 310. The ends of the track define the ends of travel of the base 400.

The base 400 can have any number of different shapes including a rectangular or square shape as shown.

As shown, one end (e.g., the proximal end) of the base 400 includes a first support member or wall 410. The wall 410 is a vertical wall that extends upwardly from the base 400. The wall 410 can extend across the entire width of the base 400 as shown. The wall 410 can also include an opening 413 (FIG. 2), such as a circular opening as shown. The opening 413 can be configured to allow the stylet to pass therethrough.

Within the interior of the handle body 310, a second support member or wall 420 can be provided. The second support member 420 can be attached to the proximal end of the stylet so as to permit the stylet to move relative to the combined inner tube/outer cannula, to facilitate extending the stylet further into the targeted tissue prior to releasing the combined inner tube/outer cannula into the tissue. However, in practice when activated, the needle projects the combined inner tube/outer cannula over the steadfast stylet. As understood, the stylet is used to initially locate and target the tissue to be biopsied in that the distal end of the stylet is placed into intimate contact with the target tissue.

The second support wall 420 is preferably parallel to the first wall 410. The second support wall 420 is oriented proximal to the first wall 410. The second support wall 420 can engage a lock mechanism that ensures that the second support wall 420 remains in a locked position. For example, a latch mechanism or the like can be used to lock the second support wall 420 in place. The handle body 310 can be constructed such that the second support wall 420 can be removed from the handle body 310 as by being removed through an opening formed in the handle body 310. Once the combined inner tube 120/outer cannula 130 project forward as described herein, the stylet can be removed to then allow removal of the captured tissue. Alternatively, the stylet remains in place and functions as a extracting dowel member which forces the tissue specimen from the internal aspect of the inner tube as the combined inner tube/outer cannula assembly is displaced back into the handle assembly for reactivation.

Before proceeding to an explanation of the other operable components of the spring loaded mechanism, it is helpful to understand that generally the inner tube 120 and outer cannula 130 are positionable between two positions, namely, a fully retracted position and a fully extended position. In the fully retracted position, the inner tube 120 and outer cannula 130 are reset back into the handle body 310 and a biasing element(s) of the spring loaded mechanism stores energy. In contrast, after the user activates the spring loaded mechanism, the biasing element releases its energy and an axial force is applied to the inner and outer tube structure in a direction away from the handle body 310, forcing the inner and outer tube structure into the tissue to be sampled.

In both the fully retracted and fully extended positions, the protrusion 135 is mated to the groove 124 coupled to one another, as described below, so that a force applied to one of the inner tube 120 and the outer cannula 130 is translated to the other of the inner tube 120 and outer cannula 130.

In order to generate a force that is sufficient to shear the soft tissue, the spring loaded mechanism includes a first biasing element 320, such as a coil spring, that applies a force against a face of the first wall 410. The size and/or location of the first biasing element 320 is selected such that the first biasing element 320 has a greater diameter than the opening 311, therefore lying outside the opening.

The first biasing element 320 is disposed between the first wall 410 and the second wall 420. The second wall 420 can be fixed in place such that the first biasing element 320 can be compressed between the two walls 410, 420 by moving the base 400 in a direction towards the second wall 420 since the base 400 is axially movable. The first biasing element 320 thus represents the means for axially projecting the combined inner tube 120/outer cannula 130.

The first biasing element 320 can be in the form of a spring (e.g., coil spring) that can store energy as well as other energy storing element(s). When the first biasing element 320 releases its energy, the spring exerts a force against the second support wall 420 to cause the axial movement of the entire base 400 in a distal direction since the second support wall 420 is attached to the base 400.

The device 100 also includes a means for causing the selective rotation of the inner tube 120 relative to the outer cannula 130. In particular, the means is in the form of a curvilinear tube 150 (which can be thought of as an inner driven structure). The curvilinear tube 150 has a first end 152 and an opposing second end 154. The curvilinear tube 150 is sized and configured to seat along the upper surface 406 of the base 400 and more particularly, the curvilinear tube 150 is disposed within the concave surface 407 of the upper surface 406 of the base 400. As described herein, the curvilinear tube 150 is axially movable within the concave surface 407 of the base 400. While the inner surface of the curvilinear tube is generally cylindrical, the outer surface need not be cylindrical and can take one of many shapes, even cube like in nature, as long as the tube can be displaced axially along the surface 406 within a complementary shaped indentation.

The curvilinear tube 150 is coupled to the inner tube 120 such that the controlled axial displacement of the curvilinear tube 150 is translated into the controlled rotation of the inner tube 120, thereby providing the means for closing and opening the snare. The ends 152, 154 of the curvilinear tube 150 are open to allow passage of the stylet through the tube 150. In addition, the central opening of the curvilinear tube 150 allows for reception of the inner tube 120. The inner tube 120 can pass through the open first end 152 but not pass through the open second end 154 (in other words, the proximal end of the inner tube 120 is located internally within the interior of the tube 150).

The curvilinear tube 150 has an outer surface 151 and an inner surface. In one embodiment, a pin and groove mechanism is used to couple the inner tube 120 to the curvilinear tube 150. For example, the curvilinear tube 150 can include at least one groove 153 formed in the inner surface, with the groove 153 having a helical shape. It will be understood that the groove 153 can be in the form of a helical slot formed through the tube. The inner tube 120 includes at least one complementary pin 155 that is configured to be received within the groove 153. In one embodiment, the inner tube 120 can have a single pin 155 or the inner tube 120 can have a pair of pins 155 that are disposed opposite one another (180 degrees apart). When the inner tube 120 has a pair of pins 155, the curvilinear tube 150 has a pair of complementary slots/grooves 153 that are symmetrically opposite one another.

Each pin 155 extends radially outward from an outer surface of the inner tube 120. The pin 155 does not extend internally within the interior of the inner tube 120. In the case of having two pins 155, the pins 155 are axially aligned and extend radially outward from the outer surface of the inner tube 120 at two opposite points thereof.

Each pin 155 is received into the respective groove/slot 153 and the linear (axial) movement of the curvilinear tube 150 is translated into the pin 155 riding along the groove 153. Since the groove 153 has a helical shape, the pin 155 riding within the groove 153 causes rotation of the inner tube 120 since the curvilinear tube 150 is prevented from rotating within the handle body 310.

In yet another embodiment, the pin 155 can be associated with the curvilinear tube 150 (i.e., can protrude inwardly from the inner surface thereof) and the helical shaped groove 153 can be formed along the outer surface of the inner tube 120. As in the other embodiments, the pin 155 is received within the groove 153 and the firing of the curvilinear tube 150 causes the pin 155 to ride within and along the length of the groove 153. As in the previous embodiment, there can be more than one pin 155 and more than one corresponding groove 153 to create the desired rotation of the inner tube 120.

Any number of different mechanisms can be employed that permit the curvilinear tube 150 to move axially along the upper surface 406 of the base 400; however, the curvilinear tube 150 is prevented from rotating. Since the curvilinear tube 150 can only move in a linear direction, the inner tube 120 is the member that has rotation imparted thereto. In one embodiment, the outer surface of the curvilinear tube 150 can have a protrusion 159 extending radially outward therefrom, with the protrusion being received within a linear guide track or slot 313 313 formed in the handle body 310 (e.g., formed along a side wall of the body 310) or in the upper surface 406 of 400 or in the complimentary recess 407. The reception of the protrusion 159 within the linear track restricts the degree of motion of the tube 150 and in particular, forces the curvilinear tube 150 to only move in a linear direction along the upper surface 406 within the concave portion 407 and across the upper surface 406. In another embodiment, the protrusion 159 extending outward from the curvilinear tube 150 can be received within a linear guide slot formed in the base 400 and more particularly, formed within the concave portion 407 of the base 400. Both of these arrangements constrain the type of movement of the curvilinear tube 150 that is permissible and in particular, only allows the curvilinear tube 150 to be fired forward (linearly) and similarly retracted backwards (linearly) without it rotating around the longitudinal axis.

The device 100 also includes a second biasing mechanism 455 which serves to controllably fire the curvilinear tube 150 as part of a second stage of operation of the device. As described in detail herein, the second stage is operable after the first stage concludes. The first stage being again the forward advancement of the base 400 and the combined inner tube/outer cannula so as to drive the combined inner tube/outer cannula into the target tissue. The second biasing mechanism 455 is disposed between the proximal end of the curvilinear tube 150 and a distal face of the first wall 410. The second biasing mechanism 455 can be in the form of a spring or other elements that can reversibly store energy. Energy is stored when the spring 455 is compressed by reducing the distance between the proximal end of the curvilinear tube 150 and the first wall 410. As with the first biasing mechanism, the second biasing mechanism is positioned such that its diameter or outer aspect lies outside of the opening formed in the first wall 410 (to allow passage of the stylet).

In the initial position (loaded position) of the curvilinear tube 150, the spring 455 is compressed and stores energy. In the initial position, the curvilinear tube 150 is disposed proximally in the concave section 407 of the base 400. Under select conditions, when the second spring 455 releases its energy, the curvilinear tube 450 is propelled forward in a linear manner within the concave surface 407. The curvilinear tube 450 travels a prescribed distance that is sufficient to cause the pin(s) 155 to travel within the helical groove(s) 153 resulting in rotation being imparted to the inner tube 120 since the curvilinear tube 150 can only move linearly and axially. The pin 155 can travel the length of the groove or can travel a substantial length of the groove so long as the distance travelled is sufficient to cause the inner tube 120 to rotate sufficiently to cause activation of the snare.

The device 100 also includes a means for controllably firing both the base 400 and the curvilinear tube 150. More specifically, a first release (lock) member 500 is provided and is accessible to the user to cause the base 400 to be fired forward as a result of the release of the stored energy of the first biasing mechanism 320. The first release member 500 can take any number of different forms so long as it has a portion that is accessible to the user and has a portion that selectively engages the base 400. For example, the first release member 500 can be in physical engagement with the base 400 such that when the first release member 500 disengages the base 400, the stored energy of the first spring 320 is released. This results in the forward firing of the base 400 and also the combined inner tube/outer cannula. The first release member 500 can be in the form of a physical structure that locks the base 400 in the initial retracted position and when the physical structure is moved such that contact with the base 400 is eliminated, the base 400 is free to move linearly and the first spring 320 provides the energy to drive the base 400. In the illustrated embodiment, the first release member 500 is in the form of a movable catch 502 (claw) that engages a portion of the base 400. For example, the first release member 500 includes a first section 504 that lies outside of the handle body 310 and is accessible by the user. This first section 504 can be in the form of a button, a slider, etc. The first release member 500 has a second section 506 that is connected to the first section 504 (or is integral therewith) and represents the portion of the release member 500 that selectively engages the base 400. The second section 506 is movable, such as being pivotable, so as to allow the second section 506 and the catch (claw) 502 engaging section to be moved out of contact with the base 400 when the user manipulates the first section 504. The first release member 500 can be biased (as by a spring) such that it normally assumes one position. As described herein, a cam can be provided to facilitate the relocking of the base 400 after the two stages of operation are complete.

A second release (lock) member 510 is in the form of a physical structure that locks the curvilinear tube 150 in place along the base 400 in the initial retracted position and when the physical structure is moved such that contact with the curvilinear tube 150 is eliminated, the curvilinear tube 150 is free to move linearly and the second spring 450 provides the energy to drive the curvilinear tube 150 along the upper surface 406 of the base 400. In the illustrated embodiment, the second release member 510 is in the form of a movable catch 512 (claw or prong) that engages a portion of the curvilinear tube 150 (e.g., a front edge of the curvilinear tube).

Unlike the first release member 500, the second release member 510 is completely disposed internally within the handle body 310 and is not accessible by the user. As a result, the disengagement of the second release member 510 occurs automatically without user intervention when the base 400 reaches a certain location within the handle body 310. The second release member 510 is thus coupled to the base 400, and may be an integral part of the base 400. The second release member 510 is naturally biased in an upward position such that when the proper registration exists between the second release member 510 and the curvilinear tube 150, the second release member 510 actively engages the curvilinear tube 150 and prevents linear (longitudinal) movement thereof.

The catch 512 extends upward, possibly through an opening or slot formed in the base 400 to engage the distal end of the curvilinear tube 150. Alternatively, the curvilinear tube 150 can have a recess in which the catch 512 is received when the curvilinear tube 150 is in the retracted position and registration exists between tube 150 and the second release member 510. In the initial position of the base 400, the curvilinear tube 150 is also in the initial retracted position and the catch 512 is in engagement (intimate contact) with the distal end of the curvilinear tube 150. As the base 400 is projected (driven) forward by the release of the energy of the first spring 320, the catch 512 engages a cam surface that is located at a fixed location. When the catch 512 engages the cam surface, the catch 512 disengages from being in contact with the distal end of the curvilinear tube 150 (or disengages from a slot or recess formed in the tube 150), thereby releasing the curvilinear tube 150 and allowing the firing thereof (due to release of the stored energy of the second spring).

The base 400 is thus constructed to allow for the inclusion and operation of the second release member 510 in that during the firing of the base 400 in the first stage, the second release member 510 does not interfere with such movement of the base 400. Only when the base 400 has traveled a prescribed distance does the second release member 510 disengage from the curvilinear tube 150 resulting in the beginning of the second stage of operation.

Thus and in accordance with the present invention, the second release member 510 is not disengaged from the curvilinear tube 150 until the first stage reaches its completion or reaches its substantial completion. In other words, the curvilinear tube 150 is not advanced axially (fired forward) until the base 400 reaches its end of travel or reaches its substantial end of travel. This results in the second stage being activated after the first stage has been activated and has reached completion and consequently, the snare is only activated after the inner tube/outer cannula has been advanced into contact with the target tissue, and substantially penetrated the tissue.

The device 100 also preferably incorporates one or more stops for limiting the degree of travel of the base 400 and/or the curvilinear tube 150. For example, a first stop can be provided for stopping the base 400 and thus, terminate the forward progression (forward firing) of the base 400. The stop can be a tab or other protrusion that is located along the travel of the base 400. The stop can be located prior to the distal end of the handle body 310 so as to prevent the distal end of the base 400 from contacting the distal end (wall) of the handle body 310. A second stop is configured to limit the degree of travel of the curvilinear tube 150 along the upper surface 406 of the base 400. The second stop can take any number of different constructions including the concave section 407, which can terminate in a hard distal end edge that can act as a stop in that when the curvilinear tube 150 contacts this end edge, the axial travel of the curvilinear tube 150 ends. The second stop can alternatively be in the form of a protrusion that is located within the concave section 407. This protrusion serves to contact the end edge of the curvilinear tube 150 and prevent further axial movement in the distal direction. Yet another stop can be the end of the groove 153 formed in the curvilinear tube 150 in that when the pin 155 reaches the proximal end of the groove 153, the curvilinear tube 150 has reached its end of distal travel.

Each of these stops is designed to stop the respective movement of one of the base 400 and the curvilinear tube 150.

The device 100 can have one or more reset mechanisms that are used after the device 100 has competed both the first stage (firing of the inner tube/outer cannula into the target tissue) and the second stage (rotation of the inner tube relative to the outer cannula to cause activation of the snare). These may serve as stops for the base 400 and curvilinear tube 150, as well. In the embodiment shown in FIGS. 1-3, there are two separate reset mechanisms, namely, a first reset mechanism 600 for resetting the curvilinear tube 150 to its initial position and a second reset mechanism 610 for resetting the base 400 to its initial position.

The first reset mechanism 600 is configured to physically move the curvilinear tube 150 in the proximal direction and across the top surface 406 to the initial position. The first reset mechanism 600 can thus be a physical structure that contacts and applies a force against the curvilinear tube 150 (e.g., against the distal end thereof) and drive the curvilinear tube 150 to the initial position. However, the first reset mechanism 600 does not limit the distal projection of the base 400 or the curvilinear tube 150 and therefore does not interfere with the operation of both the base 400 and the curvilinear tube 150 (i.e., the forward firing of the base and combined inner tube/outer cannula).

The illustrated first reset mechanism 600 can be in the form of a slider 602 that travels within a guide slot 604 (linear slot) formed in the handle body 310. The slider 602 has a first section 606 that can be accessed by the user to allow the user to drive the slider 602 within the guide slot 604 and a second section 608 that extends downward from the first section 606. The second section 608 is the section that contacts and drives the distal end of the curvilinear tube 150 in the proximal direction to its reset position. The slider 602 can thus have an L shape as well as a variety of other configurations.

In one embodiment, the guide slot 604 has a length such that when the slider 602 is at a distal end thereof, the slider 602 is beyond the distalmost point of travel of the curvilinear tube 150. As a result, the slider 602 does not impede the travel (firing) of the curvilinear tube 150.

The slider 602 works by physically driving the curvilinear tube 150 in a proximal direction until the second release member 510 reengages with the curvilinear tube 150. The user can receive auditory feedback (a click noise) and/or tactile feedback (feel a clicking engagement) to indicate that the curvilinear tube 150 has been successfully reset. Once this confirmation (feedback) is received by the user, the user can then move the slider 602 in the distal direction toward a rest position thereof (which does not obstruct the subsequent firing of the curvilinear tube 150).

Similarly, the second reset mechanism 610 is configured to physically move the base 400 in the proximal direction. The second reset mechanism 610 can thus be a physical structure that contacts and applies a force against the base 400 (e.g., against the distal end thereof) and drive the base 400 to the initial position. However, the second reset mechanism 610 does not interfere with the operation of both the base 400 and the curvilinear tube 150 (i.e., the forward firing of the base and combined inner tube/outer cannula).

The illustrated second reset mechanism 610 can be in the form of a slider 612 that travels within a guide slot 614 (linear slot) formed in the handle body 310. The slider 612 has a first section 616 that can be accessed by the user to allow the user to drive the slider 612 within the guide slot 614 and a second section 618 that extends downward from the first section 616. The second section 618 is the section that contacts and drives the distal end of the base 400 in the proximal direction to its reset position. The slider 612 can thus have an L shape as well as other configurations. The locations of the two reset mechanisms 600, 610 are mutually coexistive in that the two sliders are radially offset from one another.

In one embodiment, the guide slot 614 has a length such that when the slider 612 is at a distal end thereof, the slider 612 is beyond the distalmost point of travel of the base 400. As a result, the slider 612 does not impede the travel (firing) of the base 400.

The slider 612 works by physically driving the base 400 in a proximal direction until the first release member 500 reengages with the base 400. The user can receive auditory feedback (a click noise) and/or tactile feedback (feel a clicking engagement) to indicate that the base 400 has been successfully reset. Once this confirmation (feedback) is received by the user, the user can then move the slider 612 in the distal direction toward a rest position thereof (which does not obstruct the subsequent firing of the base 400).

The operation of the device 100 is as follows. The device 100 is initially in a rest (retracted) position shown in FIG. 1. The user grasps the device 100 by the handle body 310 and then the user advances and/or places the stylet at the target tissue. The user then actuates the device by pressing, sliding or otherwise manipulating the first release member 500 thereby unlocking the base 400 and initiating the first stage of operation. The first spring 320 releases its energy and propels the base 400 in the distal direction thereby causing the combined inner tube 120/outer cannula 130 to be driven (fired) into the target tissue. This movement is shown in FIG. 2.

As described herein, the second stage automatically follows the first stage and the forward projection of the curvilinear tube 150 along the top surface 406 causes the rotation of the inner tube 120 relative to the outer cannula 130, thereby causing the winding up (activation) of the snare. This results in the tissue specimen at the target site being captured. The device 100 can then be removed from the patient's body and then the first and second reset mechanisms can be actuated to cause the resetting of the curvilinear tube 150 which results in the snare opening to allow the user to retrieve the captured specimen. FIG. 3 shows the device 100 after completion of the first and second stages.

Figure 4:
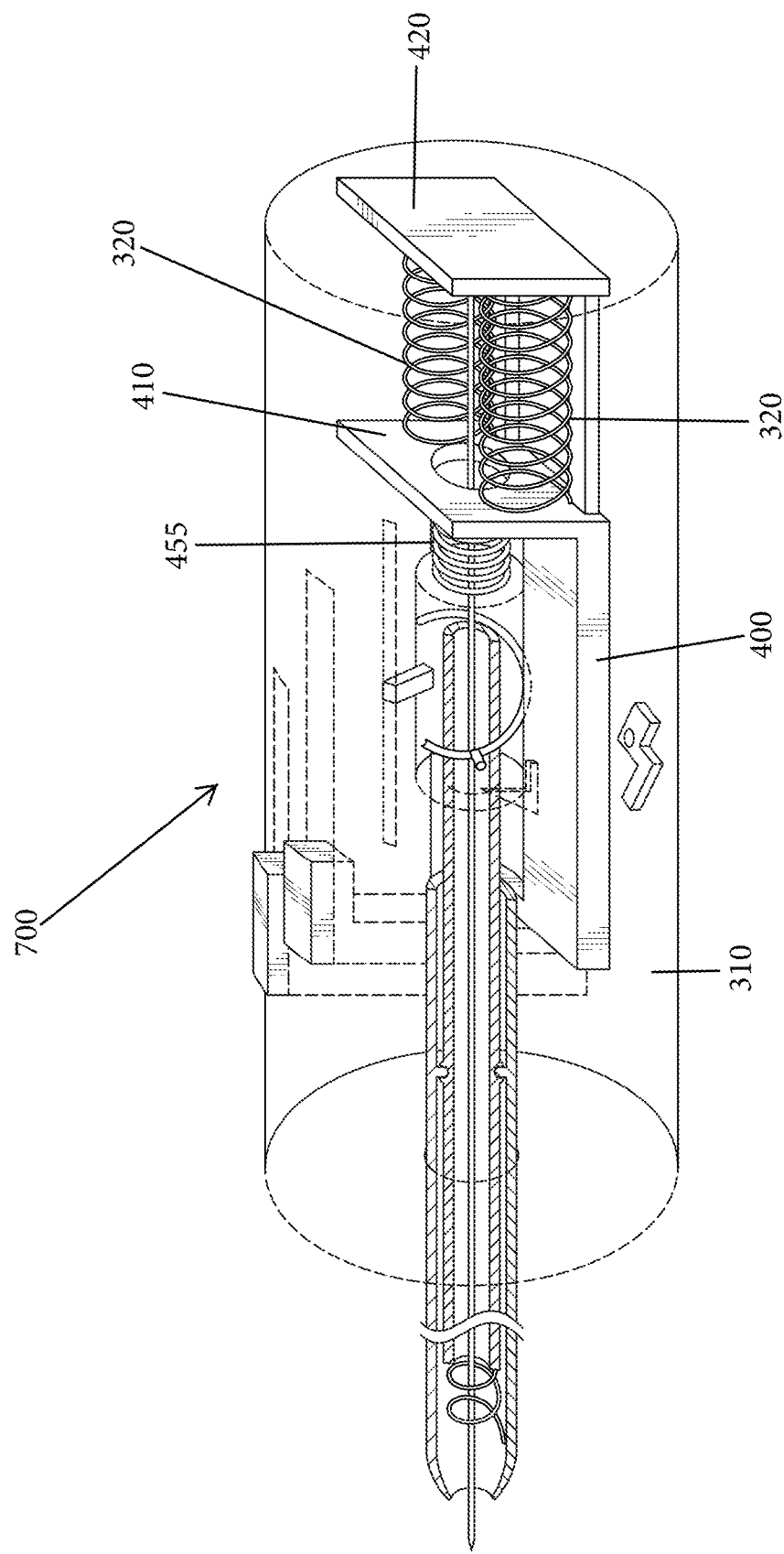
FIG. 4 is a side perspective view of a biopsy device according to a second embodiment.
Figure 5:
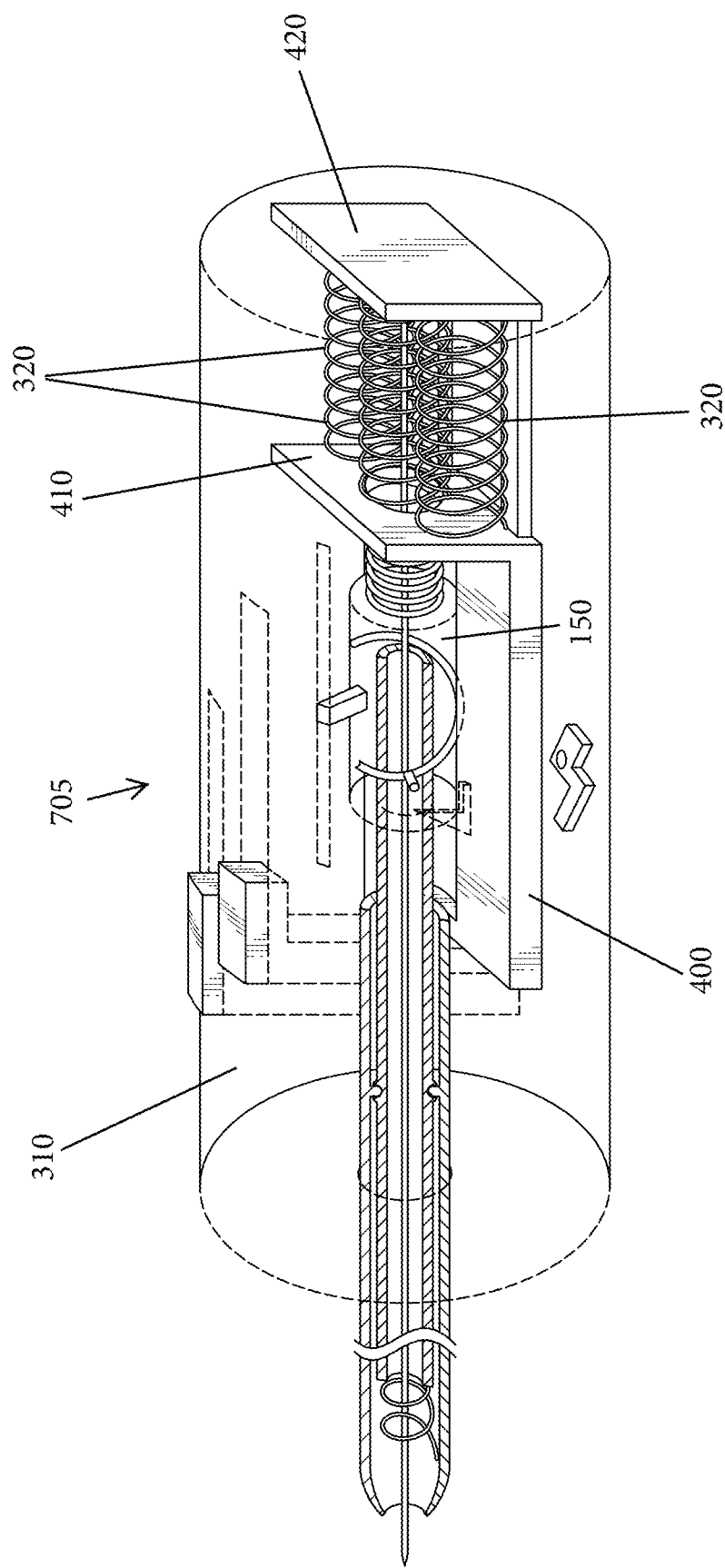
FIG. 5 is a side perspective view of a biopsy device according to a third embodiment.

FIG. 4 shows a device 700 that is similar to the device 100 with the exception that the device 700 includes two first springs 320. The two springs 320 are disposed side-by-side with the two springs 320 being disposed outside (lateral) to the opening 413 formed in the wall 410. The use of two springs 320 provides increased biasing force to drive the inner tube/outer cannula into the target tissue. FIG. 5 shows a device 705 with an additional first spring 320 and therefore, there are three total first springs to create the biasing force and propel the base 400 in the distal direction. The center spring 320 can be disposed around the opening 413 in the wall 410. As can be appreciated any number of multiple springs can be positioned between the 410 and 420 walls.

Figure 6:
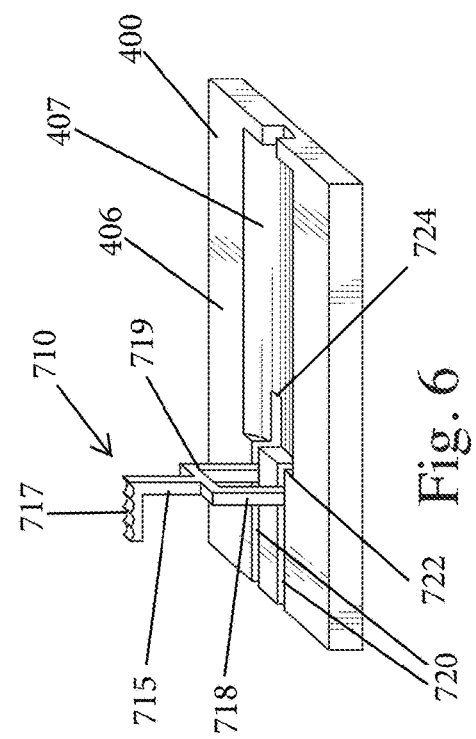
FIG. 6 is side perspective view of a reset mechanism according to one embodiment.

FIG. 6 shows a different reset mechanism 710 and in particular, the reset mechanism 710 includes a double pronged single slider 715. The slider 715 slidably travels within a pair of linear guide slots 720 formed in base 400. The slider 715 includes a first section 717 that is accessible to the user along the outside of the handle body 310. The first section 717 can be a ribbed pusher which is contacted by the user's thumb. The slider 715 has first and second prongs 718, 719 that depend downwardly from the first section 717. However, 718 and 719 could also represent the two sides of a curvilinear double pronged member, or other similar configurations. The base 40 includes a pair of guide slots 720 for receiving the two respective prongs 718, 719. The two slots 720 are open at the distal end of the base 400 and open into the concave surface at 722 and terminate at proximal ends 724. The slots 720 can pass all the way through the base 400 or can be recessed in the base 400 but not pass all the way therethrough. The slots 720 can terminate at ends 724 that are within the concave surface 407 allowing the prongs to be displaced proximally into the concave recess.

The slider 715 operates by being directed into the open ends of the slots 720 and as the slider 715 is directed in the proximal direction, the two prongs 718, 719 contact the distal end of the curvilinear tube 150 and continued driving of the slider 715 causes the curvilinear tube 150 to rest to the initial position. Once the curvilinear tube 150 is displaced proximally, continued driving of the slider 715 results in the prongs 718, 719 contacting the closed ends 724 and thus, continued driving of the slider 715 causes the entire base 400 to move in the proximal direction. Once the base 400 resets to the initial position, the slider 715 can then be moved in the distal direction.

Figure 7:
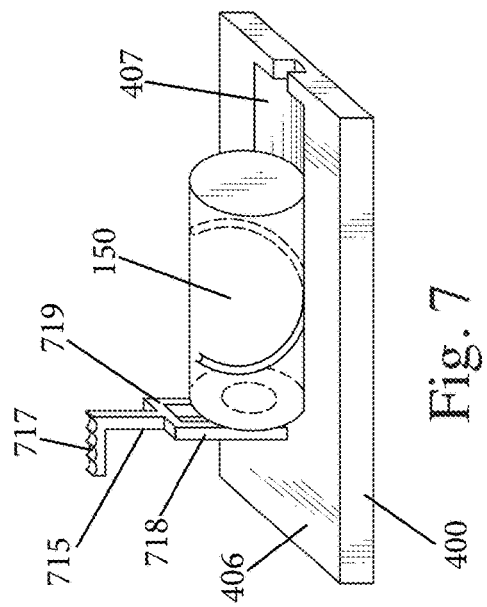
FIG. 7 is a side perspective view of a reset mechanism according to another embodiment.
Figure 8:
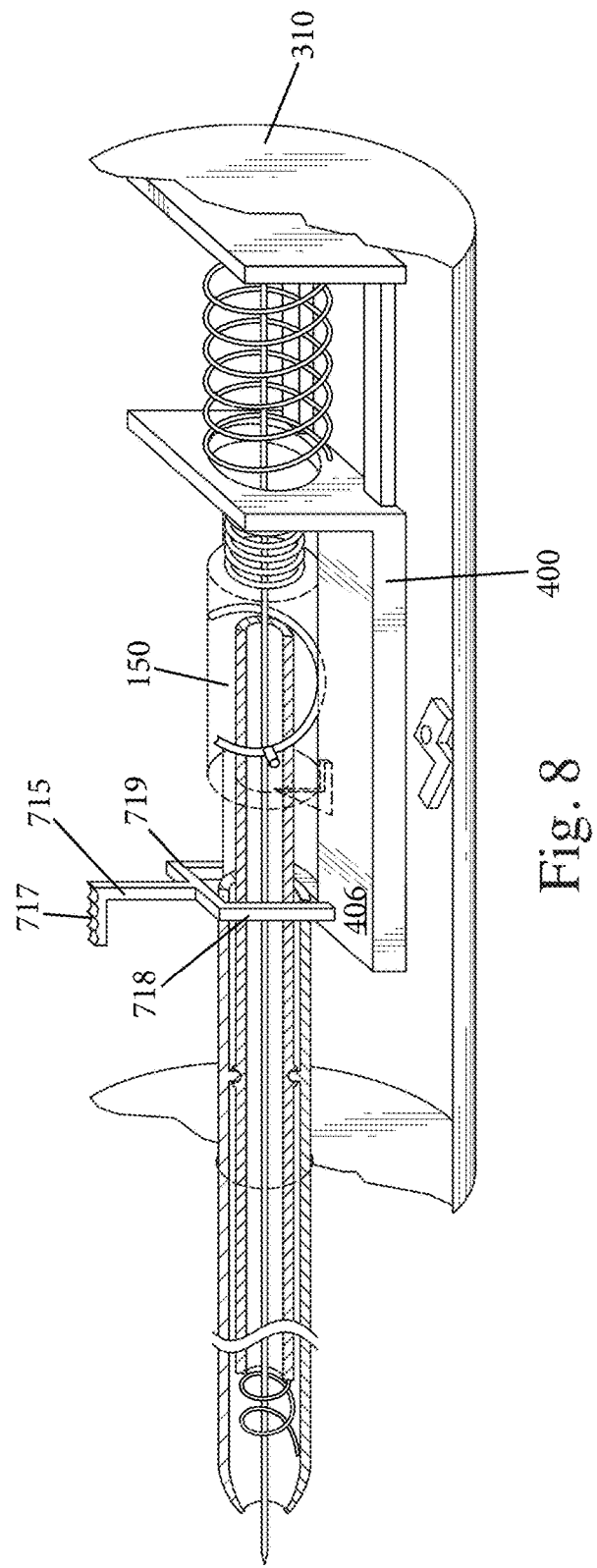
FIG. 8 is a side perspective view of a reset mechanism being shown in a first position.

FIGS. 7 and 8 show another variation of the slider 715 in that the prongs 718, 719 are disposed above the upper surface 406 of the base 400 but are spaced and positioned such that the prongs 718, 719 contact the distal end of the curvilinear tube 150. The driving of the slider 715 in the proximal direction results in the prongs 718, 719 passing over the upper surface 406 and then into contact with the curvilinear tube 150. Continued driving of the slider 715 causes movement of the curvilinear tube 150 in the proximal direction until it is reset. The proximal end of the concave section 407 can include a stop (such as a tab or lip) and therefore, when the curvilinear tube 150 is driven into contact with this stop, the continued driving of the slider 715 in the proximal direction causes the resetting of the base 400 since the stop is part of the base 400 and driving of the tube 150 against the stop causes a driving of the base 400 in the proximal direction.

FIG. 8 shows the slider 715 in a first position spaced from the base 400 and curvilinear tube 150 and FIG. 7 shows a second position, in which the slider 715 is in contact with the curvilinear tube 150. As shown in FIGS. 7 and 8, the length of the concave section 407 can be customized.

Figure 9:
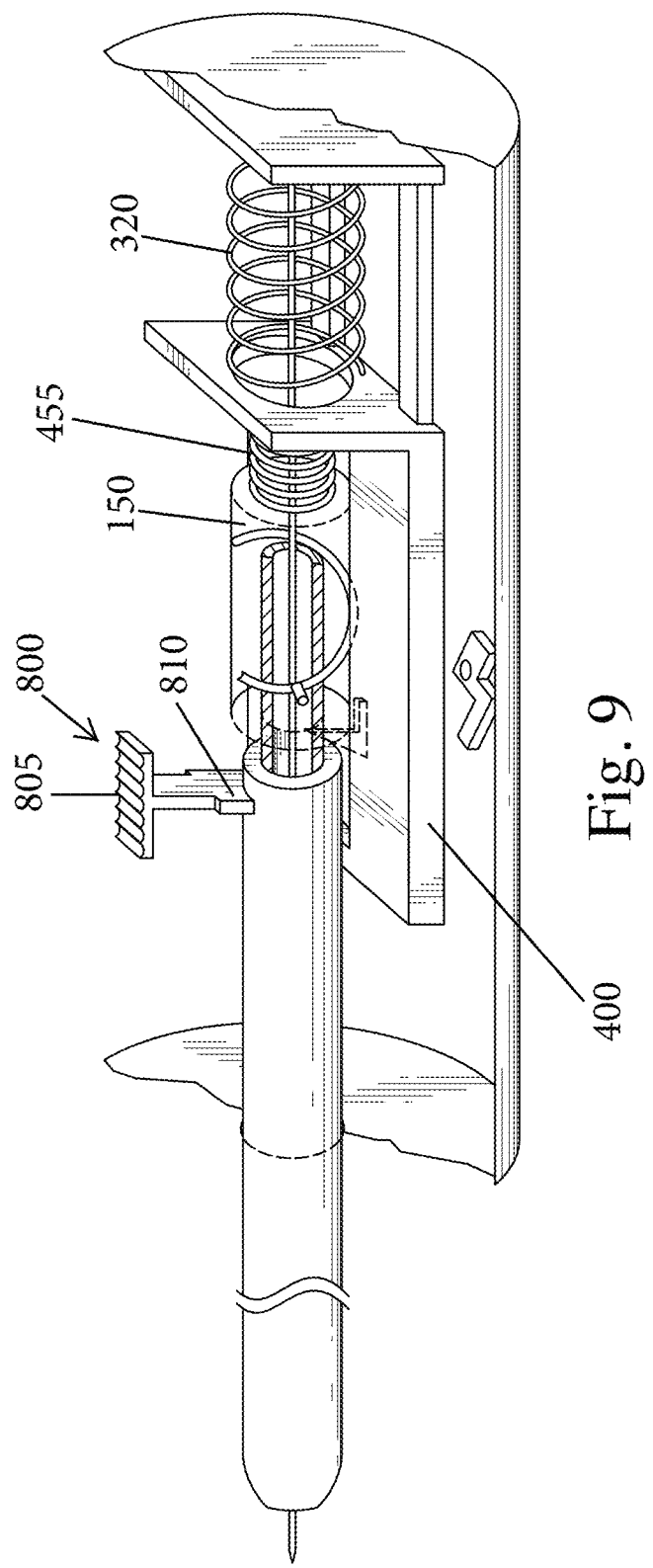
FIG. 9 is a side perspective view of a reset mechanism according to another embodiment in a first position.

FIG. 9 shows a different reset mechanism 800 in the form of a single pronged single slider. The configuration is similar to the mechanism shown in FIG. 1 except for the fact that instead of including two sliders to sequentially reposition the curvilinear tube 150 and then the base 400, one slider 805 is used. The slider 805 has one projecting element or prong 810. Unlike the previous embodiment, the prong 810 does not move within a track within the base 400 since it is positioned superior to the outer cannula 130. The prong 810 first engages the superior portion of the curvilinear tube 150. After repositioning the curvilinear tube 150 which then is locked into place by the re-engagement of the releasing lever (which is positioned inferior to the tube), continuing to apply force to the curvilinear tube 150 transmits the translational force to the base 400 which is then rebiased into its fireable position.

In order that a substantial force is not applied to the releasing lever during the re-biasing of the base 400, the curvilinear tube 150 can come to rest against a type of ledge in the base 400 which keeps it from translating beyond a certain position on the sled 400 when it is in its rebiased position.

Now referring to FIGS. 10-47 in which a biopsy device 1000 (specimen retrieving and capturing device or biopsy needle) of a snare coil design is illustrated and is configured to retrieve a target specimen which can be in the form of a tissue specimen that is located in certain organs or anatomical structures. To facilitate entry of the biopsy/capturing device 1000 into organs or anatomical structures, the device 1000 can incorporate a catheter system.

Referring now to FIGS. 10-47, the retrieval device (biopsy needle) 1000 according to another exemplary embodiment is illustrated. The biopsy needle 1000 includes an inner tube 1020 (See, FIG. 47) with a snare coil 1200 (See, FIG. 47) at a distal end thereof, an outer cannula 1030, a stylet 1001 and a handle assembly 1300. In one aspect of the present invention, the handle assembly 1300 includes a biasing (spring loaded) mechanism described in greater detail below that permits the user to selectively actuate the biopsy needle 1000 so that the outer cannula 1030 and the inner tube 1020 are rapidly advanced beyond the stylet 1001 to provide a shearing action of the soft tissue specimen.

The snare coil 1200 can comprise a coiled distal end portion of the inner tube 1020, with the snare coil 1200 being integrally formed with the rest of the inner tube 1020. For example, the inner tube 1020 can be cut (e.g., laser cut) after manufacture of the tube to form a coiled structure with the free distal end of the last coil then being attached to the outer cannula 1030 using traditional techniques, such as a heat weld, etc. The snare coil 1200 can thus have a strip like configuration. The snare coil 1200 is designed to cut the tissue and also hold and grasp the cut tissue. FIG. 47 thus generally shows the snare coil 1200 and such representation is not limiting of the present invention. For example, the width of the individual coils can vary and can be thinner or wider depending on the application. As mentioned, the number of coils in the snare coil 1200 can vary depending on the application and the construction of the needle.

It will be understood that the biopsy needle 1000 includes a needle assembly (shown in FIG. 47) that is identical or very similar to the one disclosed in FIG. 1 in that the outer cannula 1030 surrounds the inner tube 1020 and the stylet 1001 is configured to pass through the inner tube 1020. The distal end 1021 of the inner tube 1020 is connected to the distal end 1031 of the outer cannula 1030 by the snare coil 1200 that as described herein can be wound down so as to grasp and hold a tissue specimen. The needle assembly can thus generally be thought to include the inner tube 1020, outer cannula 1030 and the snare coil 1200, which constitute the parts of the needle assembly that move, while the stylet 1001, as described herein, is designed to be stationary.

Handle Construction

Figure 10:
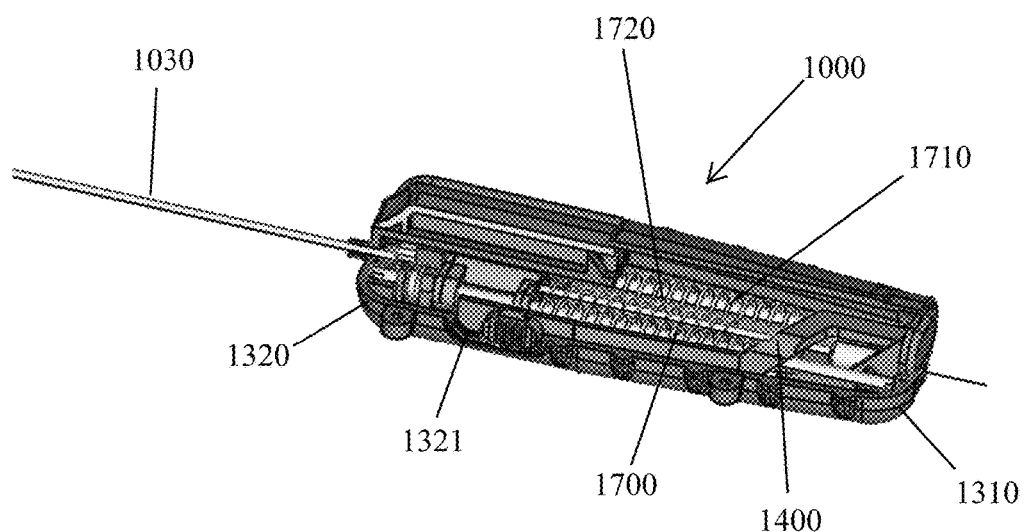
FIGS. 10-15 show various views of a biopsy device according to yet another embodiment with certain parts being removed to allow other parts to be viewed.
Figure 11:
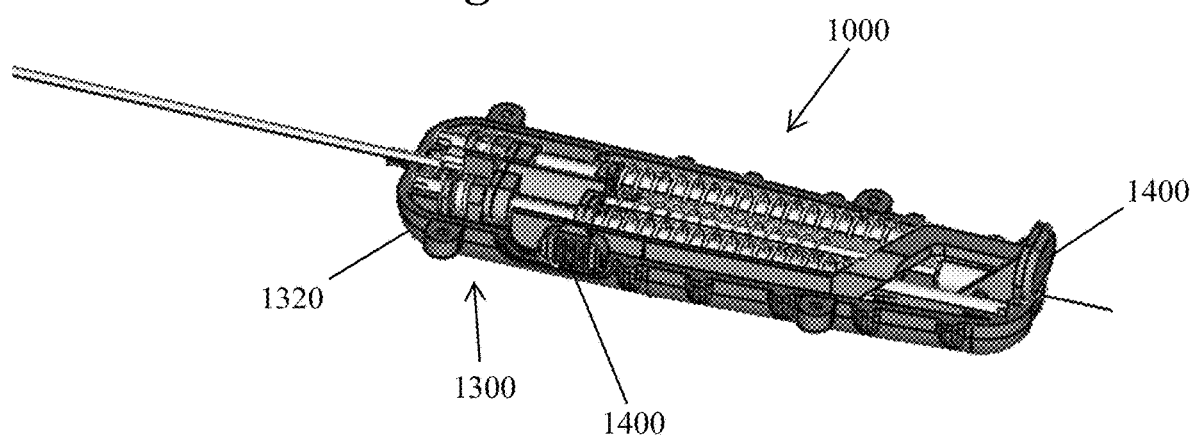
Figure 12:
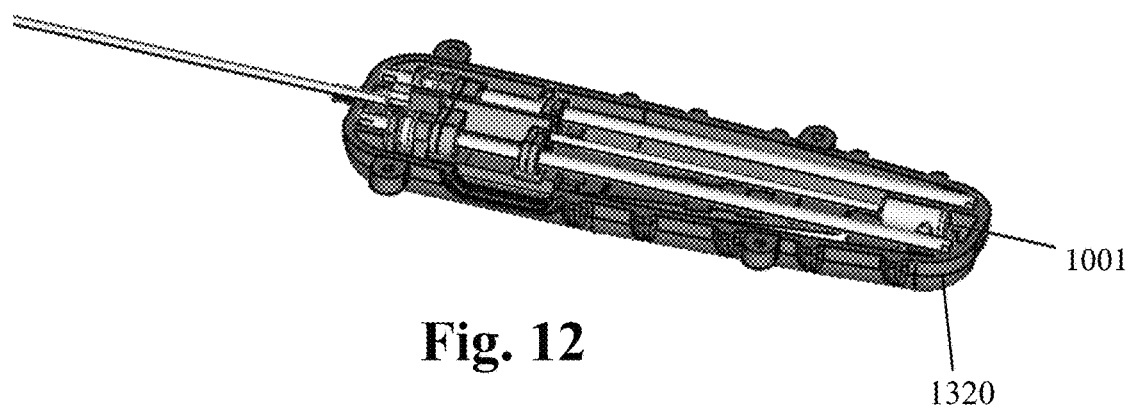
Figure 13:
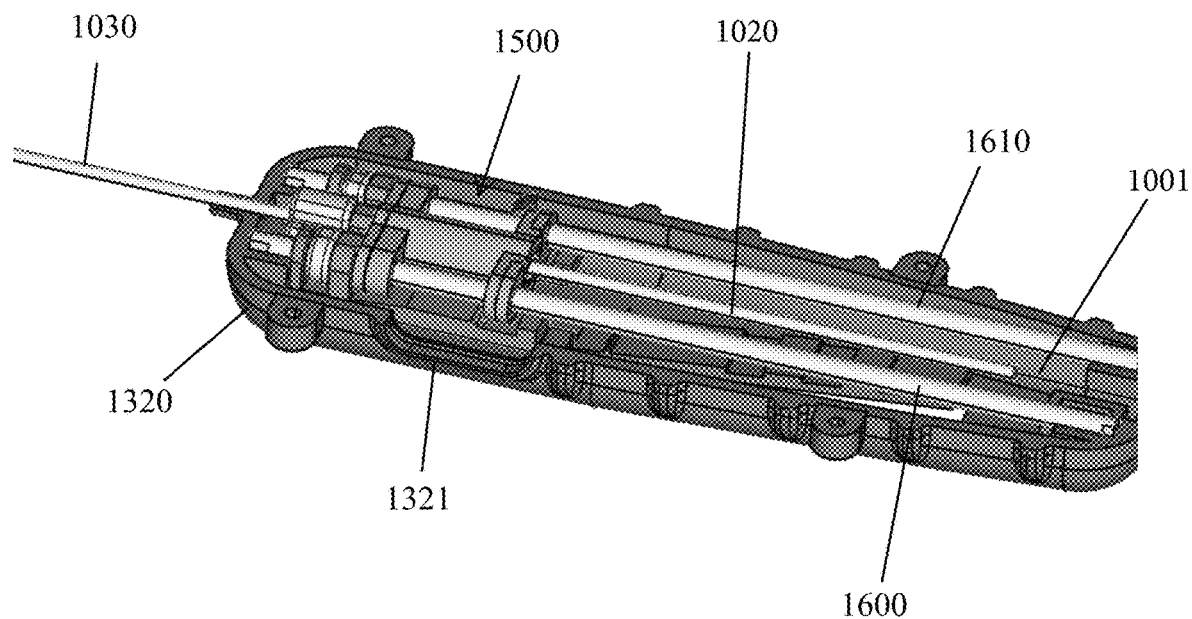
Figure 14:
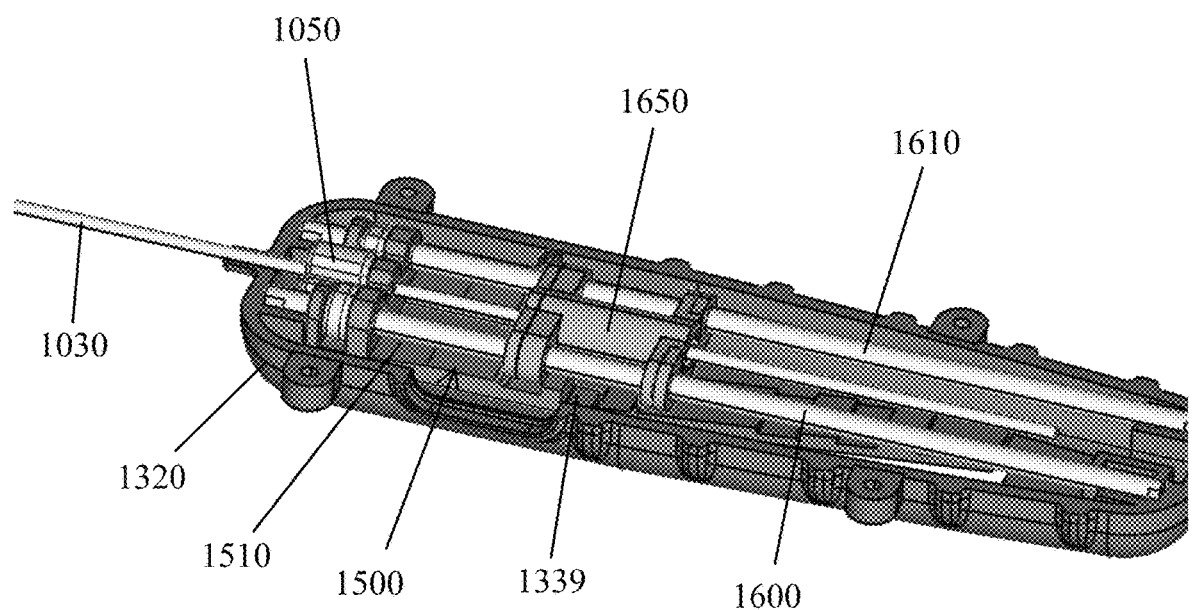
Figure 15:
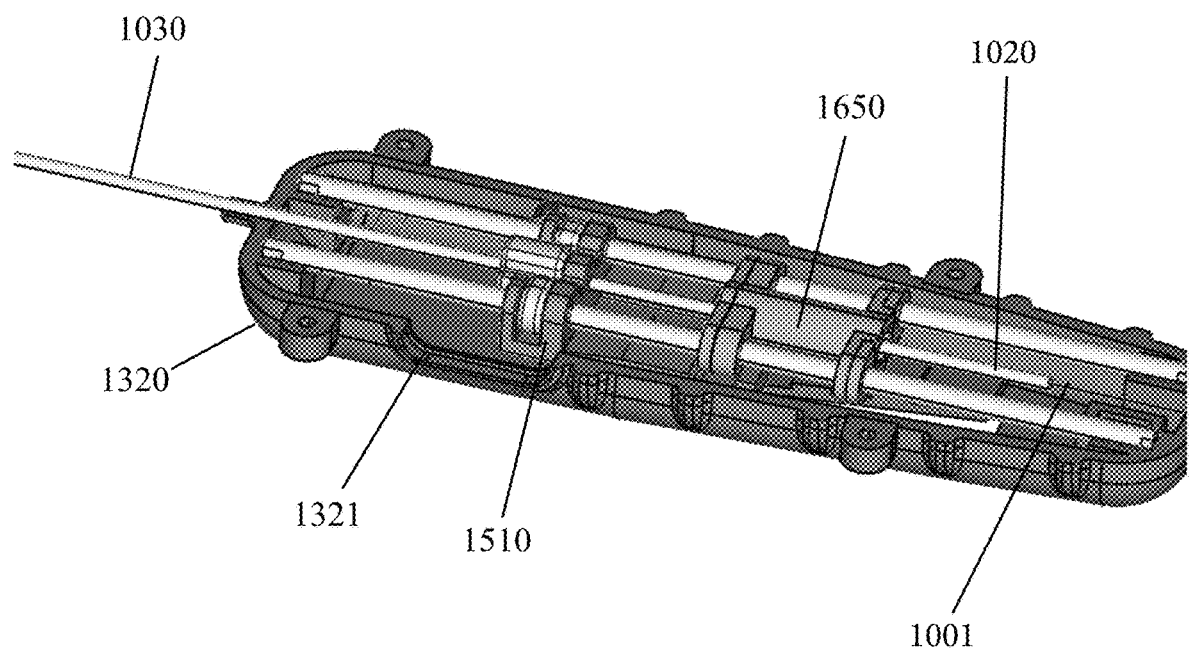
Figure 16:
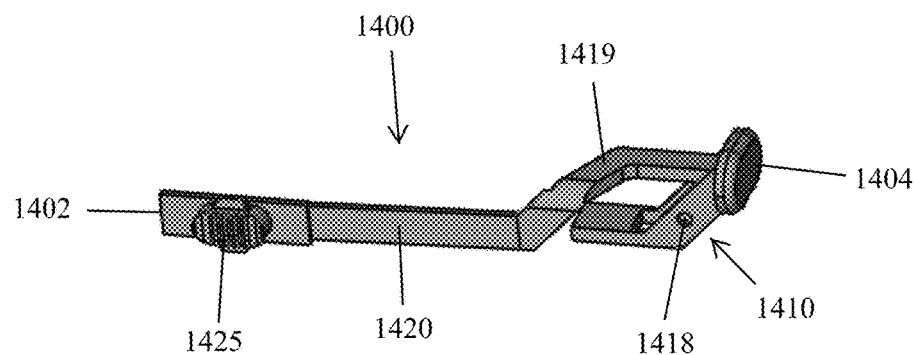
FIGS. 16-23 show various views of a first actuator that is coupled to a stylet and is part of a latch mechanism for releasing the needle assembly.
Figure 17:
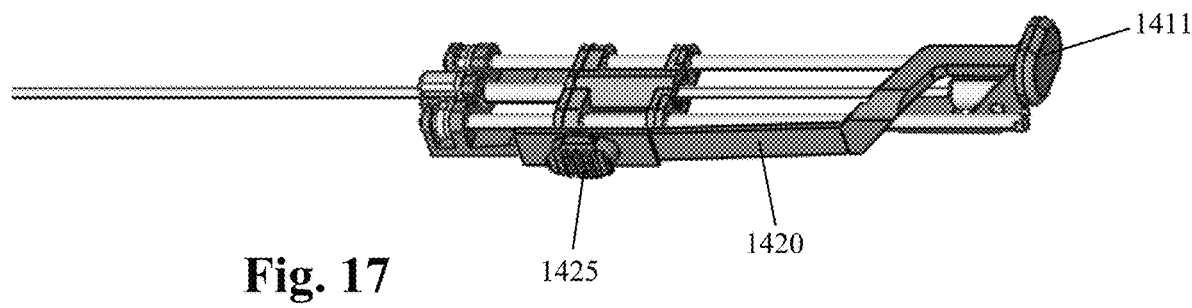
Figure 18:
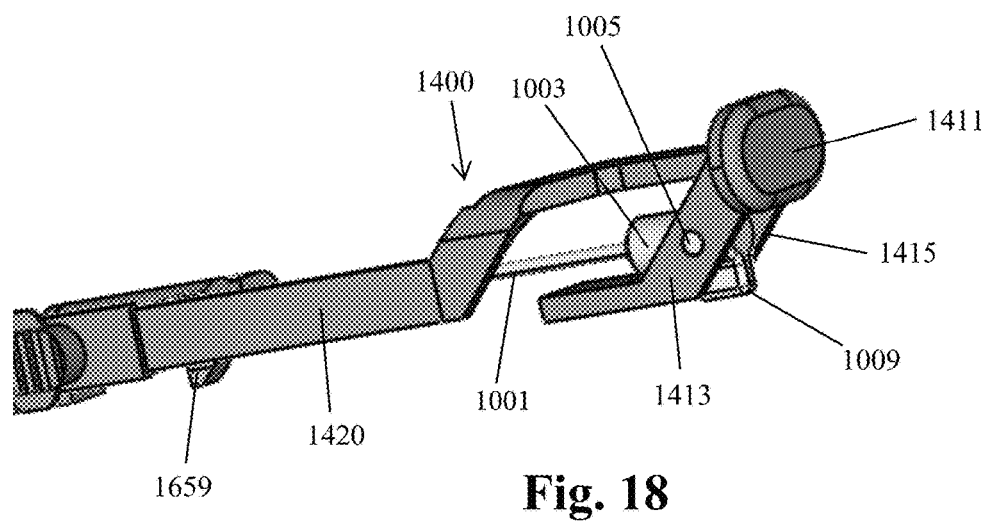

The present biopsy needle 1000 is particularly constructed for soft tissue biopsy applications since the spring-loaded mechanism provides an improved means of removing the tissue after it is cored as well as providing an improvement in the way that the tissue is acquired by the biopsy needle 1000. The handle assembly 1300 includes a handle body 1310 that can be formed in a number of different shapes and sizes and is generally a hollow body that contains the spring-loaded mechanism. For purpose of illustration only, the handle body 1310 of FIG. 10 is a generally rectangular or cylindrical or square body; however, handle body 1310 preferably is an ergonomically pleasing shape that allows for secure grasping and accurate positioning of the needle tip by the operator. Typically, the handle body 1310 is formed of several parts, such as, a first part (first half) 1320 and a second part 1325 (second half) (FIG. 36), each of which is a hollow member that receives and contains the various working parts of the device 1000. In the illustrated embodiment, the first part 1320 is a bottom half and the second part 1325 is a top half. Any number of different techniques can be used to couple the two parts including but not limited to the use of fasteners, such as screws, etc.

Each of the first part 1320 and the second part 1325 has a first (distal) end and an opposite second (proximal) end. The first part 1320 also includes a number of openings that accommodate other working parts. For example, one side wall of the first part 1320 includes a slot 1321 that accommodates a first actuator 1400 described below.

First Actuator

As described and illustrated herein, the first actuator 1400 can be in the form of a push or slide button that is configured to activate (fire) the needle assembly from an initial fully cocked position. More specifically and as best shown in FIGS. 16-23, the first actuator 1400 can be in the form of a single integral piece (e.g., molded plastic piece) that includes two portions that can be contacted and manipulated by the user for moving the first actuator 1400. The first actuator 1400 can be an elongated structure that has a first (distal) end 1402 and an opposing second (proximal) end 1404. The first actuator 1400 includes a proximal portion 1410 that includes a first button 1411 that is attached to a first rail 1413 and a second rail 1415 that is spaced from the first rail 1413 so as to define a slot 1416 therebetween. Each of the rails 1413, 1415 has a first portion that extends in a longitudinal direction and an angled portion that extends between the first portion and the first button 1411. Each of the angled portions has a hole 1418 for anchoring to a stylet 1001.

The illustrated first button 1411 has an oval or oblong shape; however, other shapes are equally possible. The first button 1411 represents the proximal most portion of the first actuator 1400.

The first actuator 1400 has an elongated distal rail 1420 that extends to the distal end 1402. The distal rail 1420 is connected to the proximal portion 1410 by a cross over rail structure 1419 that is disposed within the slot 1416 between the rails 1413, 1415. The cross over rail structure 1419 is coupled to and between the angled portions of the rails 1413, 1415. The attachment of the cross over rail structure 1419 to the rails 1413, 1415 is at a location above the holes 1418 in the angled portions. The distal rail 1420 is positioned outside of the first rail 1413.

Along the distal rail 1420 is a second button 1425. The second button 1425 can be a ribbed button that is configured for placement and longitudinal movement within the slot 1321 of the housing. As shown, the first button 1411 is oriented within a plane that is generally perpendicular to a second plane that contains the second button 1425. Since the first actuator 1400 is a single part, one will understand that it can be moved by a user by applying two different forces thereto. First, the first actuator 1400 can be moved within the housing by pushing the first button 1411 in an inward direction which is a direction toward the distal end of the handle (housing) or alternatively, the first actuator 1400 can be moved within the housing by sliding the second button 1425 within the slot 1321. Thus, applying a force to either the first button 1411 or the second button 1425 causes movement of the first actuator 1400.

As with the previous embodiment, the biopsy needle 1000 operates as a multi-stage firing needle in which the inner tube 1020 and the outer cannula 1030 first advance forward into the tissue and then the inner tube 1020 rotates relative to the outer cannula 1030 to cause a winding down of the snare coil 1200. As described herein, the movement of the first actuator 1400 initiates the firing (forward movement) of the biopsy needle 1000.

In accordance with the present invention, the first actuator 1400 also is anchored to the inner stylet 1001. As shown in the figures, the inner stylet 1001 is an elongated structure that extends distally beyond the housing. The first actuator 1400 is fixedly attached to the inner stylet 1001. The inner stylet 1001 does not move during operation of the biopsy needle 1000. As shown in the figures, a proximal end 1003 of the inner stylet 1001 can be enlarged relative to the other portion and can be in the form of a cylinder that includes one or more pins 1005 that are received within the holes 1418 of the two rails 1413, 1415 and thus is received within the slot 1416 between the rails 1413, 1415. The stylet 1001 can have two pins 1005 that are directly opposite one another and integral to the proximal end 1003 and extend radially outward therefrom in opposite directions on two opposing sides of the proximal end 1003 of the stylet 1001.

Figure 19:
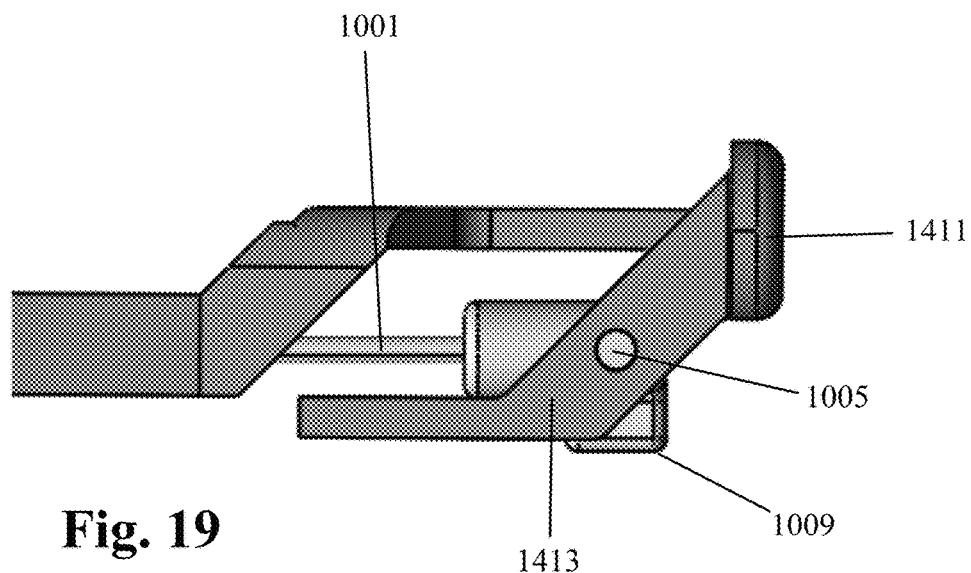

In addition and from the side views of FIGS. 19-21, it can be seen that the proximal end 1003 of the stylet 1001 includes a tab or protrusion 1009 (fin) that extends downwardly therefrom and extends below the rails 1413, 1415 of the first actuator 1400. The bottom part 1320 of the housing includes a slot 1430 that receives the tab 1009 of the stylet 1001 when the biopsy needle 1000 is assembled.

Figure 20:
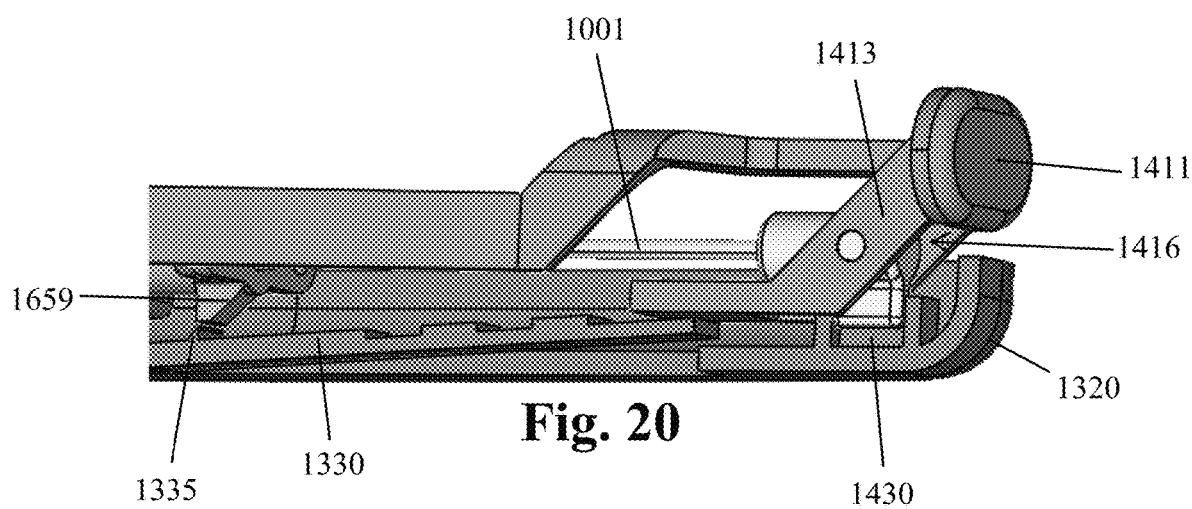
Figure 21:
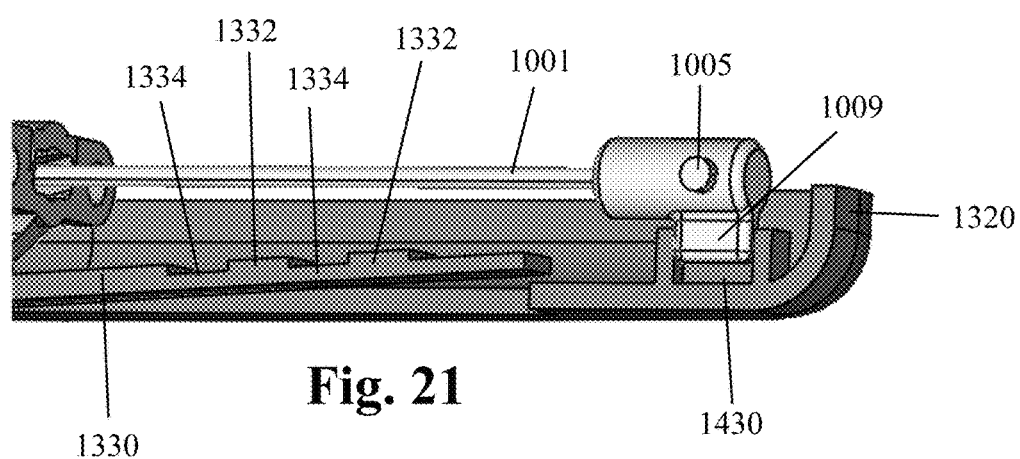
Figure 22:
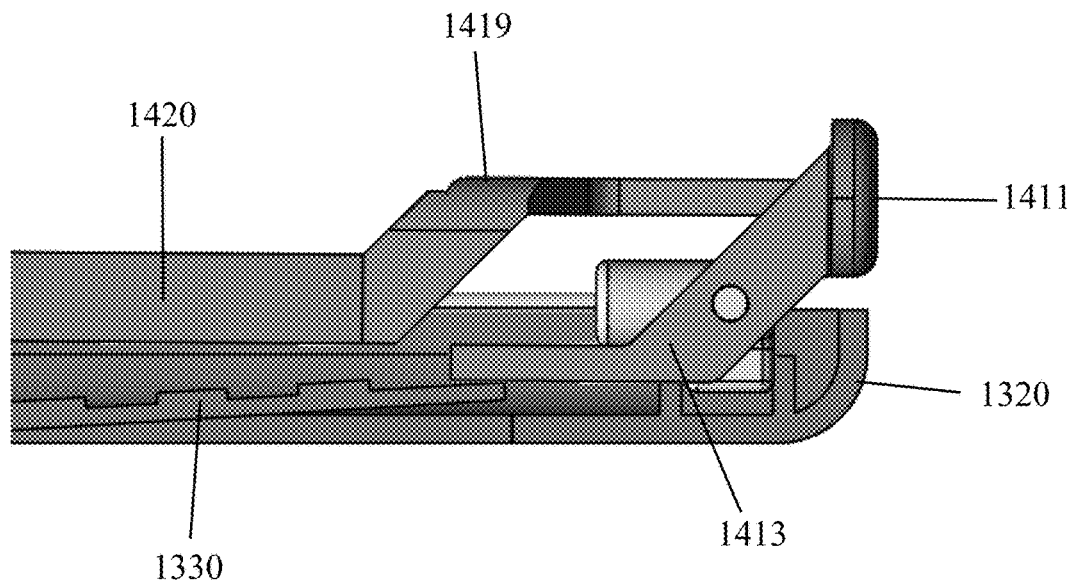
Figure 23:
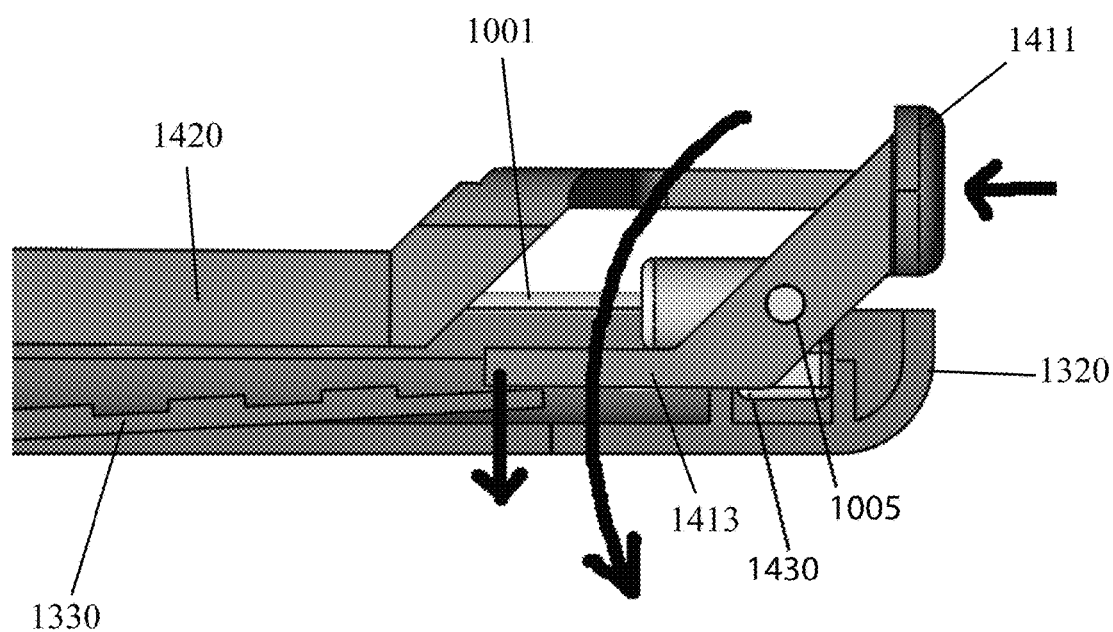
Figure 24:
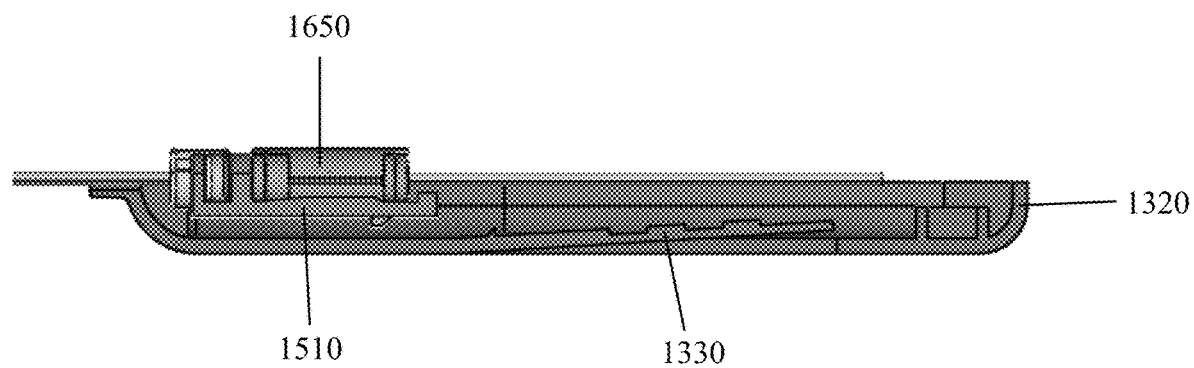
FIGS. 24-31 show various operating states of the needle assembly and a second actuator that causes controlled axial movement and rotation of the needle assembly.
Figure 25:
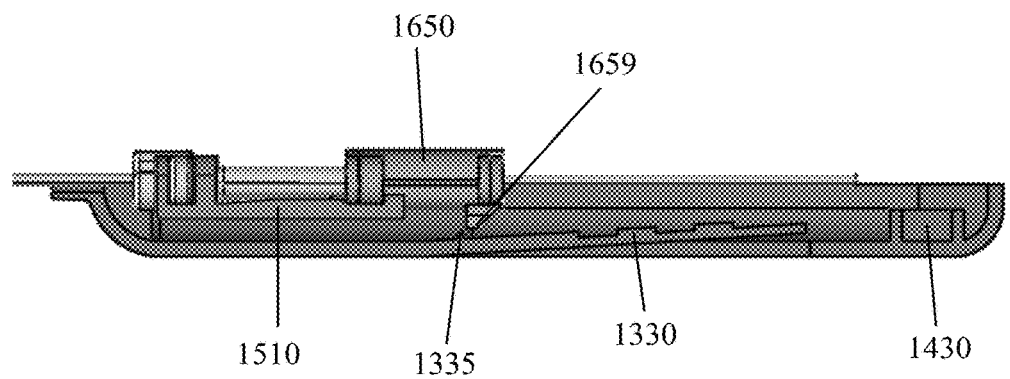

As shown in FIGS. 20-22, when the first actuator 1400 is pushed forward, the tab 1009 of the stylet 1001 which is disposed within the slot 1430 restrains forward movement of the first actuator 1400. As best illustrated in FIG. 23, the forward directed force applied to the first actuator 1400 causes the first actuator 1400 to rotate about the pin 1005 that attaches the first actuator 1400 to the inner stylet 1001. The pin 1005 thus acts as pivot (fulcrum) and since the first button 1411 is located above the pivot (pin 1005), a forward axial force applied to the first button 1411 will cause a downward movement of the rails 1413, 1415 due to the pivoting action about the pivot (fulcrum). It will be understood that since the first actuator 1400 is formed as a single part, the forward sliding of the second button 1425 causes the same pivoting action about the pivot (pin 1005) resulting in the downward movement of the rails 1413, 1415.

Thus, this rotation of the first actuator 1400 in turn contacts and pushes down a flexible locking member (a flexible leg/cantilevered structure) 1330 of the first part 1320 of the housing. The flexible locking member 1330 is located along and is an integral part of the floor of the first part 1320 and can be referred to as a ladder like structure due to the fact that the flexible locking member 1330 includes a series of raised peaks 1332 and valleys 1334 located between the peaks 1332 (FIG. 21). The valleys 1334 can be thought of as being recesses or notches formed along the ladder. The flexible locking member 1330 is a cantilevered structure and therefore, when a downward force is applied to a free end of the flexible locking member 1330, the flexible locking member 1330 flexes downward. The flexible locking member 1330 is thus a biased structure in that when an applied force is removed, the flexible locking member 1330 will return to its original raised position. The flexible locking member 1330 can also include a raised protrusion (catch) 1335 (FIG. 20) that is closer to the connected end of the flexible locking member 1330. The function of the raised protrusion (catch) 1335 is described later.

Needle Firing Mechanism

As described herein, the movement of the flexible locking member 1330 in a downward direction results in a release of a second actuator 1500 that is configured to both axially advance the inner tube 1020 and outer cannula 1030 and then subsequently cause the controlled rotation of the inner tube 1020 relative to the outer cannula 1030. The second actuator 1500 can be thought of as a firing mechanism that causes the controlled axial firing of the inner tube 1020 and outer cannula 1030 and subsequent rotation of the inner tube 1020. As shown in the figures, the second actuator 1500 includes a movable base 1510 that is driven axially (longitudinally) within the housing as described herein.

Both the inner tube 1020 and the outer cannula 1030 are axially movable through the displacement of the movable base 1510 which can be thought of as being a sled-like structure that is controllably moved an axial defined distance within the hollow interior of the housing 1310.

As best shown in FIGS. 27-34, the base 1510 has a first (distal) end 1502, an opposing second (proximal) end 1504, a top surface 1506 and an opposing bottom surface 1508. The base 1510 generally has a U-shaped structure in that it is defined by a first flexible leg 1520, an opposing second flexible leg 1530 and an integral cross member 1540 that extends between and connects the first leg 1520 to the second leg 1530. The first and second legs 1520, 1530 thus are in the form of cantilevered structures that have a degree of flexing action. Between the legs 1520, 1530 is open space, thus defining the U-shaped structure.

As shown in the figures, the movable base 1510 travels along first and second guides 1600, 1610. The movable base 1510 is permitted to move along the first and second guides 1600, 1610 in both a first (forward) direction and a second (rearward) direction. The first and second guides 1600, 1610 are securely and fixedly attached to the housing and extend in a longitudinal direction. In the illustrated embodiment, the first and second guides 1600, 1610 are in the form of elongated rods that are attached at their ends to the housing and are oriented parallel to one another with a space therebetween to accommodate working parts of the needle assembly. As shown in the figures, the first part 1320 of the housing includes molded slots in which the ends of each of the first and second guides 1600, 1610 are received for coupling the first and second guides 1600, 1610 to the housing.

The cross member 1540 includes a first protrusion 1541 formed at one end thereof and includes a first through hole formed therein and a second protrusion 1542 formed at the opposite end thereof and including a second through hole. The first through hole receives the first guide 1600 and the second through hole receives the second guide 1610. In this manner, the movable base 1510 slides in a longitudinal direction along the first and second guides 1600, 1610. The first protrusion 1541 can be formed of two spaced apart fingers that extend upwardly from and are perpendicular to the top surface 1506. A slot 1543 is formed between the two spaced apart fingers that define the first protrusion 1541. Each of these spaced apart fingers includes a though hole that is axially aligned with the other and receives the first guide 1600. Similarly, the second protrusion 1542 can be formed of two spaced apart fingers that extend upwardly from and are perpendicular to the top surface 1506. A slot 1544 is formed between the two spaced apart fingers that form the second protrusion 1542. Each of these spaced apart protrusions includes a though hole that is axially aligned with the other and receives the second guide 1610.

The cross member 1540 also includes a center structure 1547 that includes a hole 1548 that receives the inner tube 1020 (FIGS. 35 and 47) and stylet 1001.

The first leg 1520 is an elongated structure that has a recess (notch or slot) 1521 formed therein near the free distal end of the first leg 1520. As shown, one end wall 1523 that defines the recess 1521 is in the form of a beveled edge (ramp). The end wall 1523 is closer to the cross member 1540 than the other end wall 1525 that defines the slot 1521. The end wall 1525 can be in the form of a straight (vertical) edge.

The second leg 1530 is an elongated structure that has a recess (notch or slot) 1531 formed therein near the free distal end of the second leg 1530. Unlike the recess 1521, the recess 1531 can be defined by two vertical end walls. The second leg 1530 also includes a side tab 1539 that that is formed along one side edge of the second leg 1530 and extends vertically. The side tab 1539 can have a curved and angled top surface 1545. As shown in the figures, the side tab 1539 is disposed adjacent or at one end of the recess 1531.

As will be described herein, the first and second legs 1520, 1530 are independently acted upon during the firing mechanism and in fact, one of the legs 1520, 1530 is first deflected downward to allow a first action to occur and then the other of the legs 1520, 1530 is deflected downward to allow a second action to occur.

Needle Holder

The biopsy needle 1000 also includes a needle holder 1050 that serves to secure the needle assembly to the second actuator 1500. In particular, the needle holder 1050 is fixedly attached to the outer cannula 1030 (FIG. 35) as thus the two move in unison. The needle holder 1050 has a center portion 1051 which includes a center hole through which the stylet 1001 and inner tube 1020 can travel and pass into the lumen of the outer cannula 1030 which is secured by the holder 1050. The needle holder 1050 also has a first side extension (first lobe) 1052 extending radially outward from one side of the center portion 1051 and a second side extension (second lobe) 1053 extending radially outward from the other side of the center portion 1051. The first side extension 1052 has a hole formed therein that receives the first guide 1600 and the second side extension 1053 has a hole formed therein that receives the second guide 1610. The needle holder 1050 is thus axially movable along the first and second guides 1600, 1610.

It will also be understood that the needle holder 1050 is captured within the movable base 1510 and therefore, moves therewith. As shown, the first side extension 1052 is received within the first slot 1543 defined by the first leg 1520 and the second side extension 1053 is received within the second slot 1544 defined by the second leg 1530. The first side extension 1052 is thus sandwiched between the fingers that form the first protrusion 1541 and the second side extension 1053 is sandwiched between the fingers that form the second protrusion 1542. The passage of the first guide 1600 through the aligned holes of the first protrusion 1541 and first side extension 1052 and the passage of the second guide 1610 through the aligned holes of the second protrusion 1542 and second side extension 1053 result in the needle holder 1050 being coupled to and carried by the movable base 1510. In this manner, when the movable base 1510 is fired axially forward along the guides 1600, 1610, the needle holder 1050 and thus, the outer cannula 1030 attached thereto, are likewise driven in this axial manner and this results in the outer cannula 1030 being fired forward. It will be understood that the inner tube 1020 does not move in an axial direction relative to the outer cannula 1030 and is constrained in a fixed axial position by a sleeve 1025 (FIG. 35) that is fixedly attached to and surrounds the inner tube 1020 and is the part from which the engaging tab 1033 protrudes. As described below, the tab 1033 represents a pin component that is part of a pin and groove mechanism for imparting rotation to the inner tube 1020. In one embodiment, the sleeve 1025 can be coupled to the base 1510 such that during the first stage of operation as discussed herein, the inner tube 1020 and base 1510 move in unison (i.e., the inner tube 1020 does not have any axial movement relative to the base 1510). For example, the sleeve 1025 can have a ring or protrusion that engages a groove or notch formed in the base 1510 to cause engagement and capture of the sleeve 1025 on the movable base 1510. Thus, during the needle firing first stage, the inner tube 1020, outer tube 1030 and base 1510 all move in unison together with no relative movement therebetween. It will be understood that the sleeve 1025 could be eliminated and the tab 1033 depends from the inner tube 1020 itself.

Curvilinear Part

The biopsy needle 1000 also includes a means for causing the selective rotation of the inner tube 1020 relative to the outer cannula 1030. In particular, the means is in the form of a curvilinear part (inner driven structure) 1650 that is configured to be selectively coupled to the movable base 1510 and is driven in an axial direction along the same first and second guides 1600, 1610 that the movable base 1510 is driven along.

The curvilinear part 1650 includes a main base portion 1660 that is in the form of an elongated tube having a first end 1651 and an opposing second end 1652 with a lumen formed therein. At the first end 1651 of the base portion 1660 is a first flange 1670 (a first bilateral tab extension) that has a wing shape and is defined by first and second portions that extend outwardly from both sides of the base portion 1660 and at the second end 1652, there is a second flange 1680 (a second bilateral tab extension) that has a wing shape that has first and second portions that extend outwardly from the both sides of the base portion 1660. Each portion of each of the first and second flanges 1670, 1680 has a hole and therefore, the holes 1690 in the flange portions along one side of the main base portion 1660 are axially aligned with one another and the holes 1691 in the flange portions along the other side of the main base portion 1660 are axially aligned with one another. The first guide 1600 passes through the holes 1690 and the second guide 1610 passes through the holes 1691, thereby permitting the curvilinear part 1650 to ride along the first and second guides 1600, 1610. It will be appreciated that the reception of the first and second guides 1600, 1610 within the first and second flanges 1670, 1680 constrains the movement of the curvilinear part 1650 and in particular, the curvilinear part 1650 is prevented from rotating, while permitting axial movement of the curvilinear part 1650.

It will also be appreciated that the illustrated first and second flanges 1670, 1680 have an illustrated seam since the curvilinear part 1650 can be constructed of two parts, namely, a top piece and a bottom piece that when placed together form the inner lumen of the curvilinear piece 1650 and its associated internal groove. This allows the inner cannula hub with the circular protrusion tab 1033 to be easily placed inside the curvilinear assembly during manufacture.

As shown in the figures, each of the first flange 1670 and the second flange 1680 is configured to be received within the first and second recesses 1521, 1531 for detachably connecting the curvilinear part 1650 to the movable base 1510. When the curvilinear part 1650 is attached to the movable base 1510, the two parts can move in unison together.

The curvilinear part 1650 also include a locking tab 1659 (FIGS. 43 and 44) that protrudes downwardly therefrom and is centrally located at the proximal end of the curvilinear part 1650 (proximate second flange 1680). The locking tab 1659 can have a straight vertical edge as well as an angled edge that acts as a cam surface. As described herein, the interaction of the locking tab 1659 and the locking member 1330 allows for the curvilinear part 1650 (and the movable base 1510) to be locked in a position relative to the housing.

Figure 35:
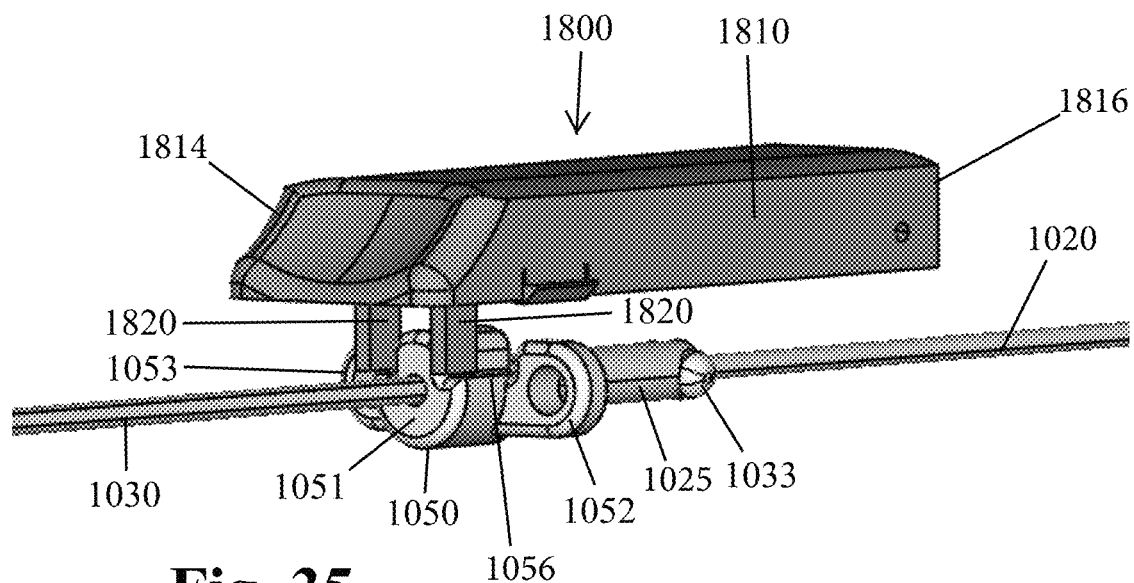
FIGS. 35-37 show the interaction between a reset button (part of a cocking mechanism) and a needle holder and the movable base.
Figure 36:
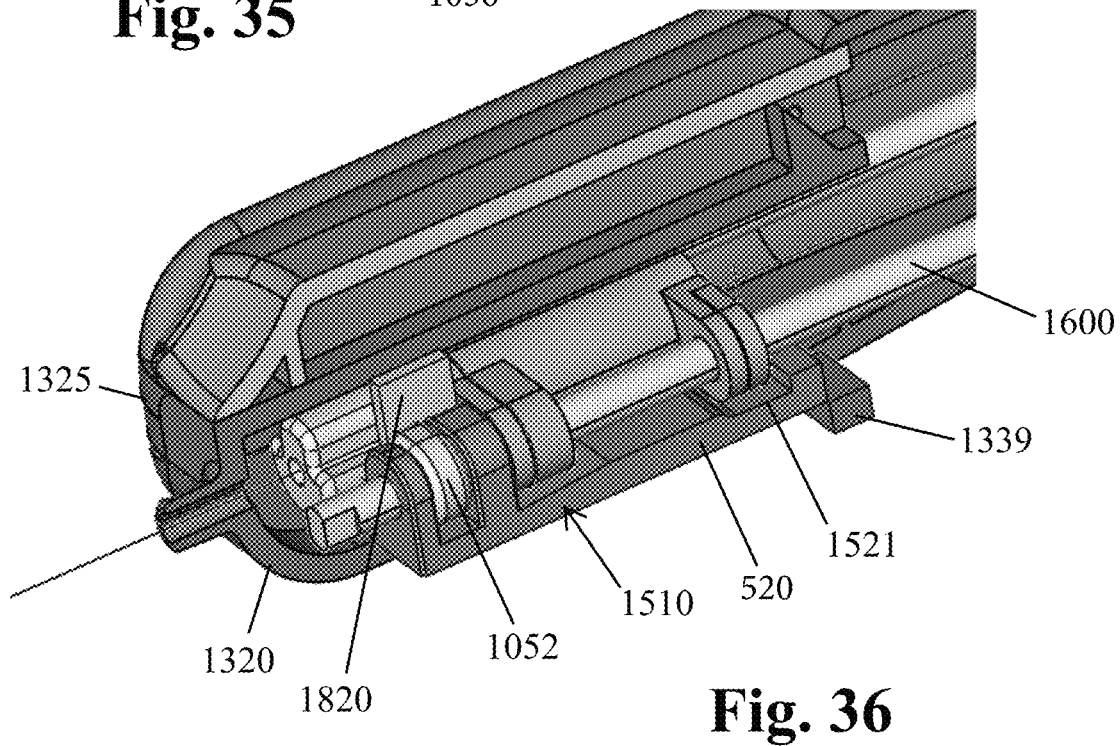
Figure 37:
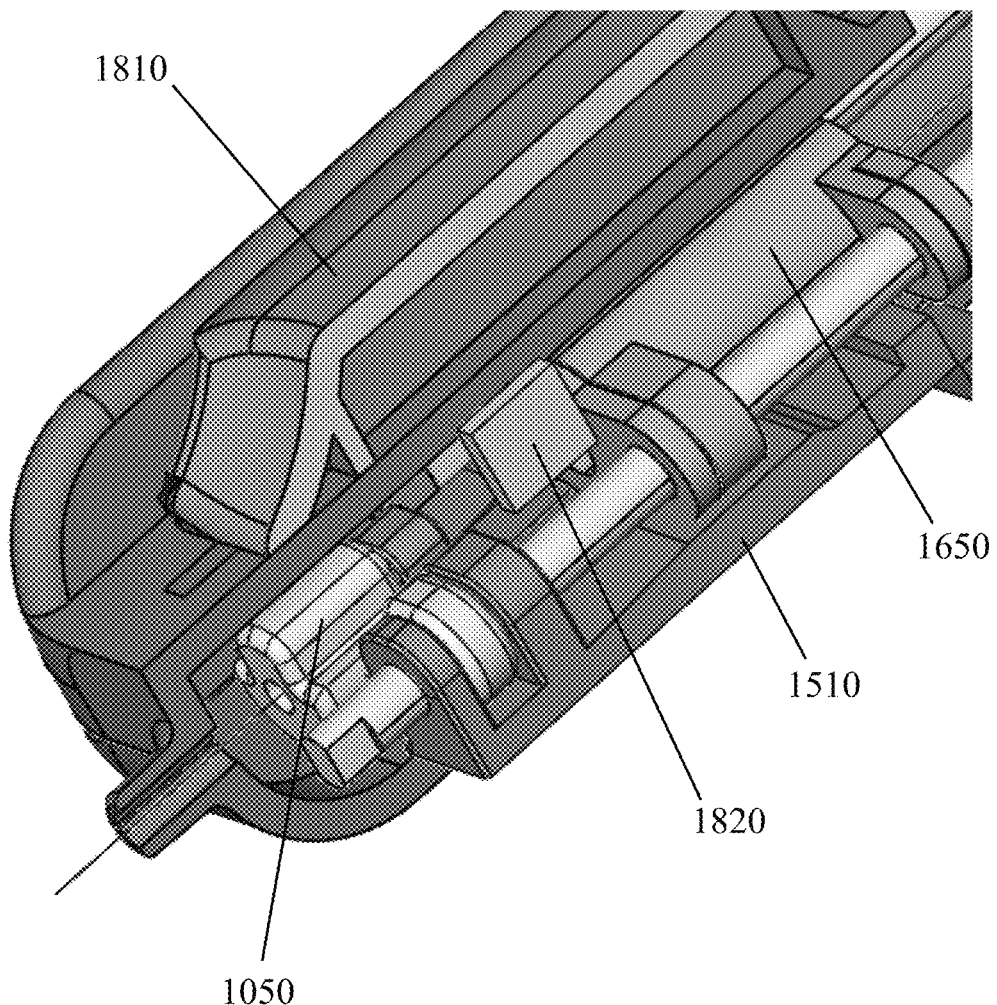
Figure 38:
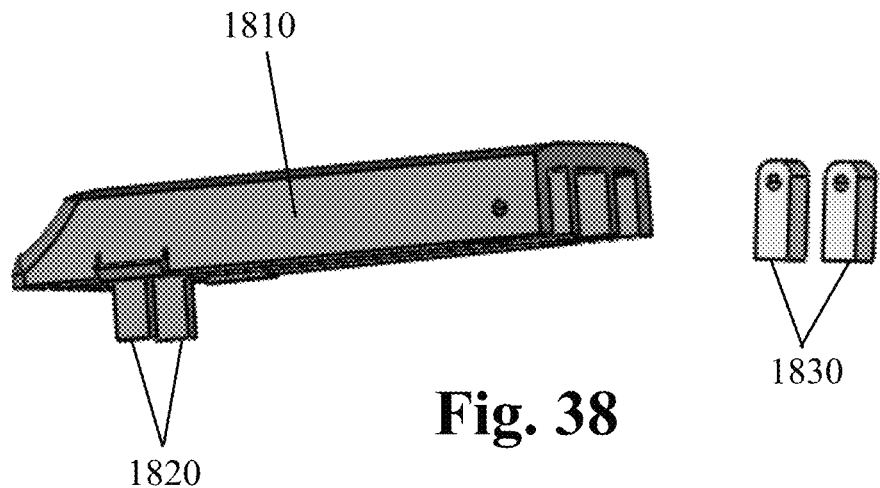
FIGS. 38-46 show various views of the reset button and its position and operation in a first cocking position and a second cocking position.
Figure 39:
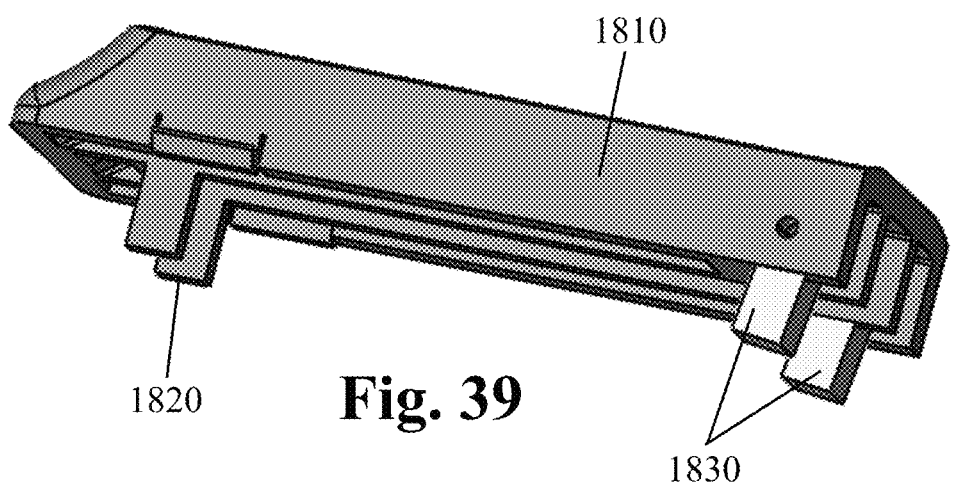
Figure 40:
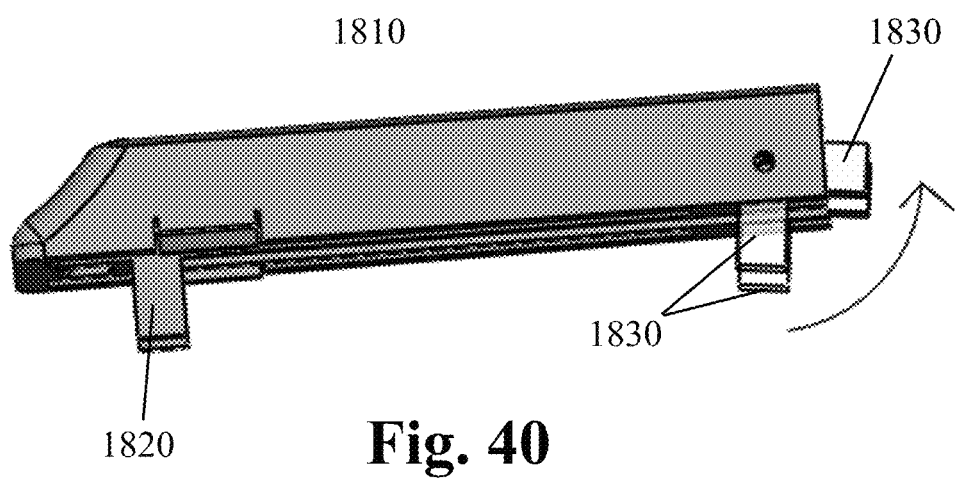

The main base portion 1660 is coupled to the inner tube 1020 in such a way that movement of the curvilinear part 1650 is translated into rotation of the inner tube 1030 when the curvilinear part 1660 moves axially relative to the inner tube 1020. For example, a pin and groove arrangement can be provided in that one of the curvilinear part 1650 and inner tube 1020 can have a pin (e.g., tab 1033 of FIG. 35) that is received in a curved groove formed in the other. For example, one end of the inner tube 1030 can have an outwardly extending pin 1033 (FIG. 35) that is received within a groove (internal curvilinear groove) formed internally within the lumen of the main base portion 1650 (e.g., see curvilinear groove 153 in FIG. 1) It will be appreciated that the pin 1033 can be formed as part of the sleeve 1025 to which the inner tube 1020 is coupled. As a result, the axial movement of the curvilinear part 1650 results in the pin 1033 traveling along the internal curvilinear groove and this results in rotation of the inner tube 1020. The pin 1033 in FIG. 35 is shown as a rounded structure to allow it to more easily travel within the curved groove. Thus, while the inner tube 1020 remains coupled to the base 1510, the curvilinear part 1650 is fired axially over the base 1510 results in the pin 1033 traveling within the curvilinear groove and this imparts spin to the inner tube 1020 only.

The lumen of the base portion 1660 also permits passage of the stylet 1001.

The biopsy needle 1000 includes a biasing mechanism for applying a biasing force to the curvilinear part 1650 to drive (fire) the curvilinear part 1650 within the housing. As described herein, during a first stage of operation, the forward movement of both the movable base 1510 and the curvilinear part 1650 cause axial advancement of both the inner tube 1020 and the outer cannula 1030 and as described herein, there is a second stage of operation in which the movement of the curvilinear part 1650 causes rotation of the inner tube 1020 relative to the outer cannula 1030.

As shown in the figures (FIGS. 10 and 11), the biasing mechanism can be in the form of a first biasing member 1700, such as a first spring, and a second biasing member 1710, such as a second spring. The first biasing member 1700 is disposed about the first guide 1600 and the second biasing member 1710 is disposed about the second guide 1610. First ends of the first and second biasing members 1700, 1710 are in contact with second flange 1680 so as to apply a biasing force to the curvilinear part 1650. This biasing force is configured to drive the curvilinear part 1650 in an axial (longitudinal) manner along the guides 1600,

1610. The second ends of the first and second biasing members 1700, 1700 can seat against stops (a wall) formed as part of the housing. When the curvilinear part 1650 is moved in a direction toward the proximal end of the housing, the first and second biasing members 1700, 1710 are compressed and store energy. A third biasing member (e.g., a spring) 1720 can be provided and surrounds the stylet 1001 and can apply a force thereto.

The first part 1320 of the housing also includes a stop 1339 that selectively engages the first leg 1520 so as to control movement of the movable base 1510. The stop 1339 is located proximate the connected end of the cantilevered structure 1330 (i.e., the flexible leg of the first part 1320).

The first leg 1520 is configured to keep the movable base 1510 and needle from sliding back until it is translated more proximally to the unfired completely cocked position. The second leg 1530 is configured to keep the curvilinear part 1650 from advancing until the movable base 1510 and curvilinear part 1650 have completed their travel. As shown, when the curvilinear part 1650 is coupled to the movable base 1510 by reception of one of the flanges 1670, 1680 in the recesses 1521, 1531 of the movable base 1510, the two parts 1510, 1650 are coupled together and move as one.

Fully Cocked Position—Ready for Firing

Figure 26:
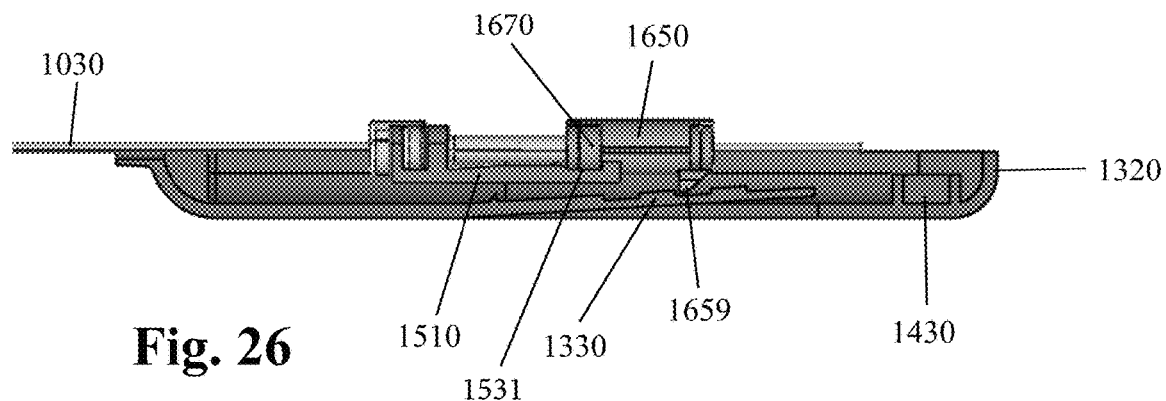
Figure 27:
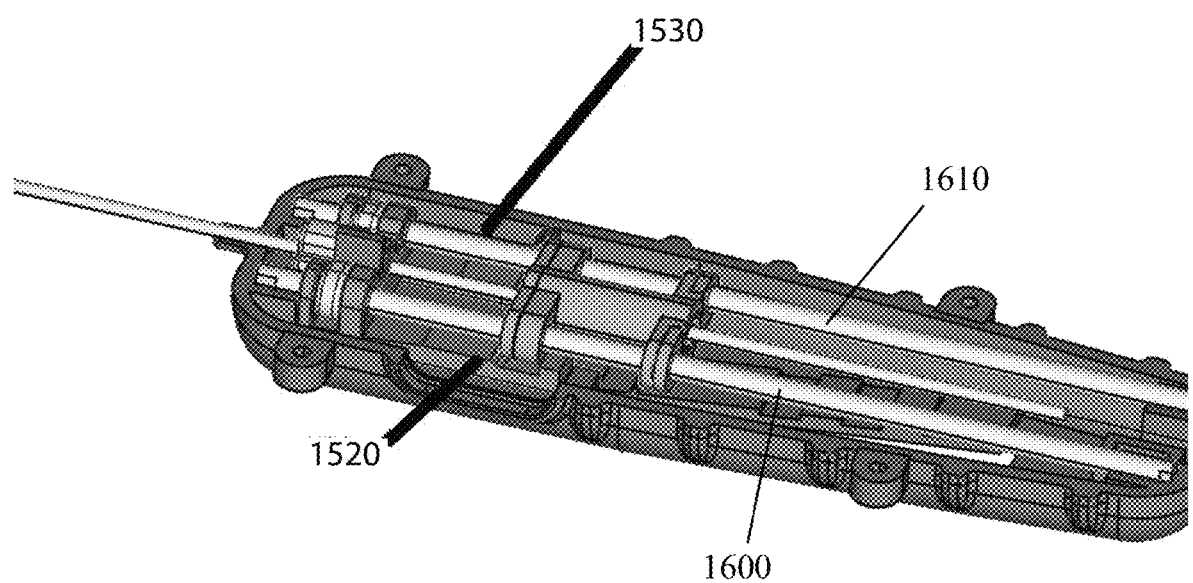
Figure 28:
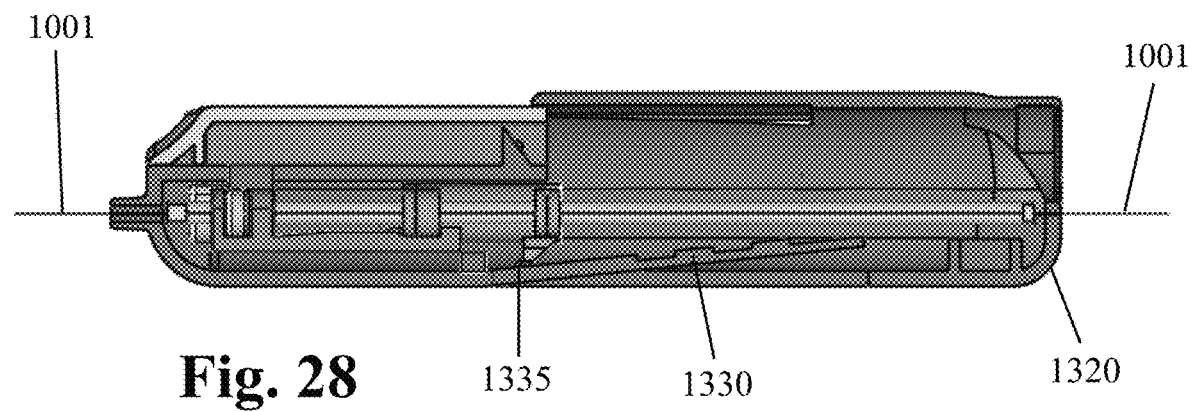
Figure 29:
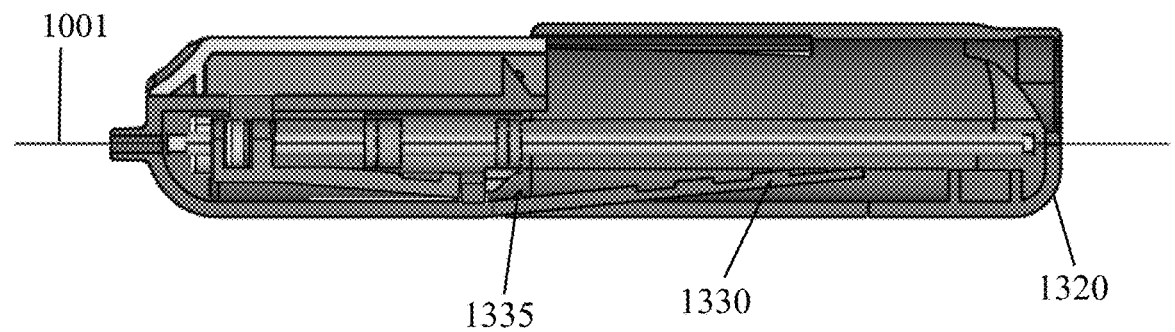
Figure 30:
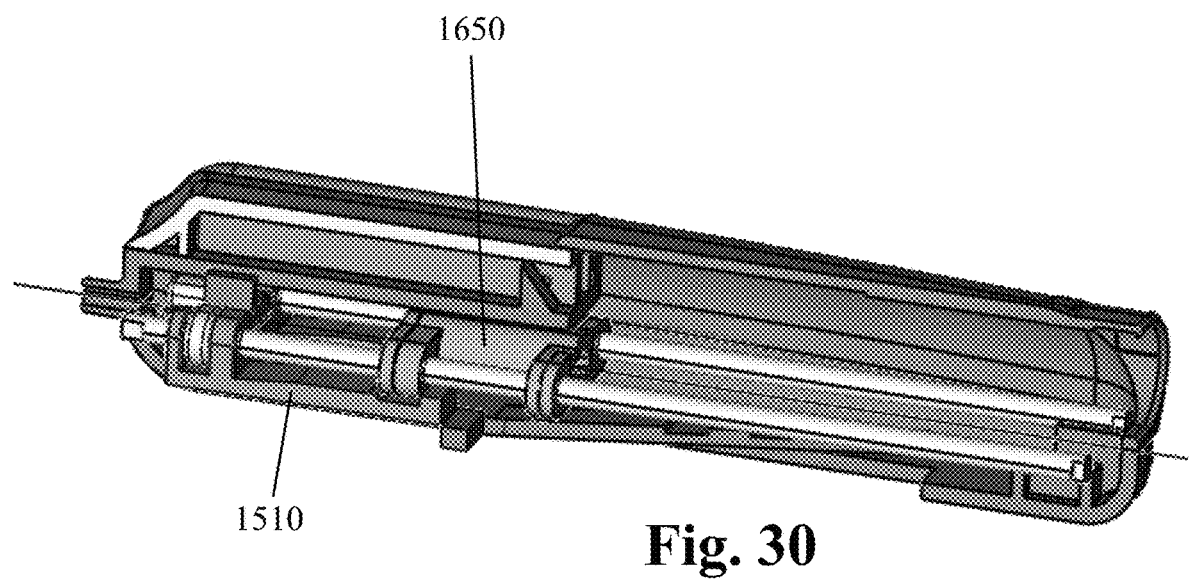

As shown in FIG. 26, in a fully cocked (ready for firing) position, the flange 1670 is disposed within the recesses 1521, 1531; the locking tab 1659 is engaged with one of the recesses 1334; and springs 1700, 1710, 1720 are compressed.

Fully Fired Position

To initiate firing of the second actuator 1500, the first actuator 1400 is manipulated by pressing the first button 1411 or sliding forward the second button 1425. As previously mentioned, this causes the rails 1413, 1415 to pivot downward and push downward on the flexible locking member (cantilevered structure) 1330. The movement of the flexible locking member 1330 results in the locking tab 1659 of the curvilinear part 1650 being disengaged from one of the recesses 1334. Once this occurs, the springs 1700, 1710, 1720 release their energy causing forward advancement of both the movable base 1510 and the curvilinear part 1650 which is engaged thereto. Once the movable base 1510 has completed its forward travel (i.e., the distal end of the movable base 1510 contacts the distal end portion of the housing), the second leg 1530 releases the curvilinear part 1650 from its engagement to the movable base 1510, thereby allowing the curvilinear part 1650 to travel axially over the now stationary movable base 1510. More specifically, as the combined movable base 1510 and curvilinear part 1650 move forward and as they reach the end of travel of the movable base 1510, the side tab 1539 associated with the second leg 1530 contacts a tab formed in the handle housing and the cam surface of the side tabs 1539 assists in causing the downward deflection of the second leg 1530, thereby releasing the curvilinear part 1650 from its fixed connection to the movable base 1510. The biasing force applied by the springs 1700, 1710 causes the curvilinear part 1650 to move axially over the stationary movable base 1510 which remains stationary at this point.

Anytime, the curvilinear part 1650 is forward to the slot 1531 of the second leg 1530, it depresses the first leg 1520 due to the geometry of the first leg 1520 as shown. In particular, once the second leg 1530 deflects downward, the disengaged curvilinear part 1650 rides up the ramp 1523 of the first leg 1520 causing deflection of the first leg 1520 in a downward direction. The curvilinear part 1650 is thus completely free of the movable base 1510 as is driven forward due to the biasing force. In addition, the second leg 1530 is further deflected downward as the curvilinear part 1650 advanced forward.

As long as the curvilinear part 1650 is forward of the stop 1339 and maximally displaced forward on the movable base 1510, the depressed first leg 1520 engages the stop 1339 and keeps the curvilinear part 1650 from retracting. It will be appreciated that during the rotation of the inner tube 1020 relative to the outer cannula 1030, the needle must be prevented from moving backward by keeping the movable base 1510 from moving backward. In other words, since the needle holder 1050 is carried by the movable base 1510, the movable base 1510 controls axial movement of the needle and preventing retraction of the movable base 1510 prevents the needle (parts 1030/1020) from moving backward.

In this second stage firing of the curvilinear part 1650, the axial movement of the curvilinear part 1650 is transferred into a rotation of the inner tube 1020 relative to the outer cannular 1030 and this causes closing of the snare and capture of the specimen.

Cocking Mechanism

The needle 1000 also includes a cocking mechanism 1800 that is used to repositionally cock the second actuator 1500 after it has been fired. As described herein, the cocking mechanism 1800 can be in the form of a two-step cocking process, namely, a first cocking position in which the curvilinear part 1650 is moved back to an "uncoiled" position and a second cocking position in which the curvilinear part 1650 is in a fully activated position ready for firing. It will be understood that the "uncoiling" of the snare coil 1200 of the inner tube 1020 is necessary in order to recover the specimen.

As shown in FIGS. 35-46, the cocking mechanism 1800 includes a lever or button 1810 that is slidably movable within the housing. The button 1810 includes a body that has a first end 1814 and an opposing second end 1816. The first end 1814 is contoured to receive a thumb or finger and permit the button 1810 to be pressed inward to cause cocking of the second actuator 1500. The button 1810 has two attributes for engaging the curvilinear part 1650 and the movable part 1510. The first attribute is two fixed legs 1820 that extend downwardly from the underside of the button 1810. The two fixed legs 1820 can be formed perpendicular to the body of the button 1810 and are parallel to one another. As described herein, the two fixed legs 1820 only engage the curvilinear piece 1650. As shown, the needle holder 1050 includes axial slots or grooves 1056 and similarly, the movable base 1510 includes axial slots or grooves both of which are configured to accommodate the fixed legs 1820 and in particular, these grooves allow the two fixed legs 1820 to pass by the movable base 1510 and the needle holder 1050 that is coupled to the movable base 1510. The curvilinear part 1650 does not have such grooves.

First Cocked Position

Figure 31:
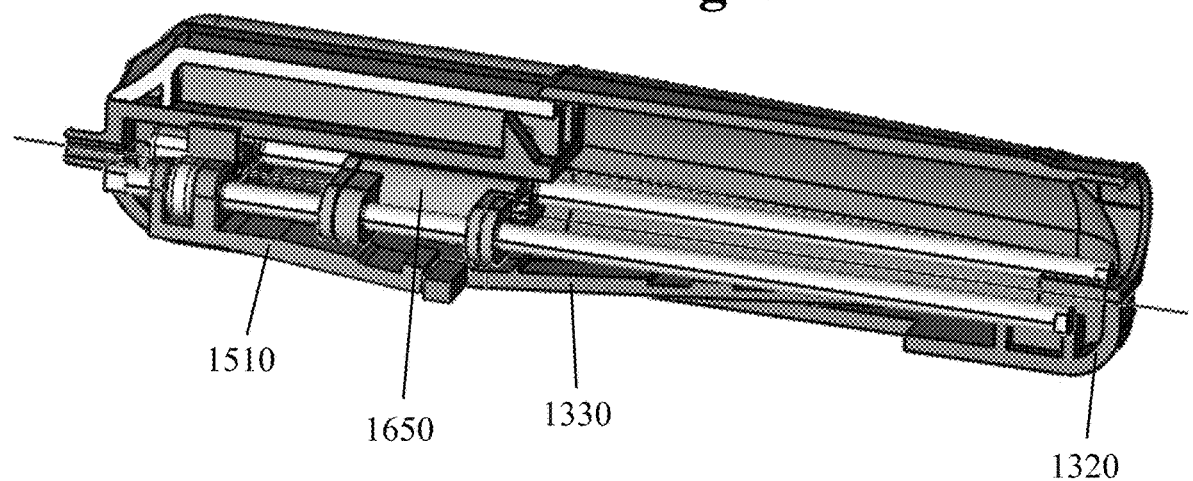
Figure 32:
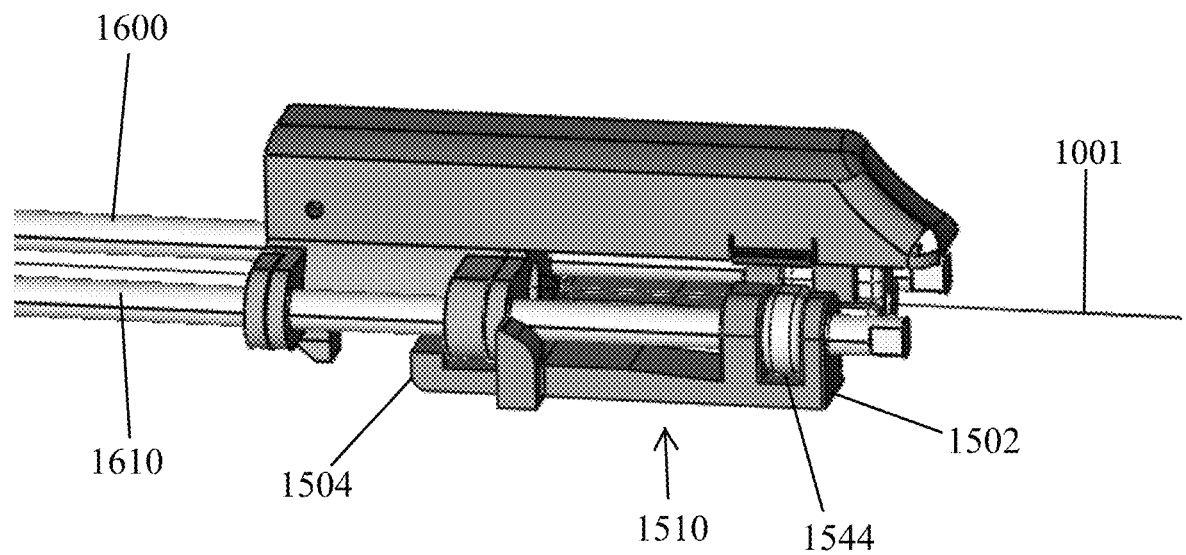
FIGS. 32-34 show various views of the second actuator that comprises a movable base and a curvilinear part.
Figure 33:
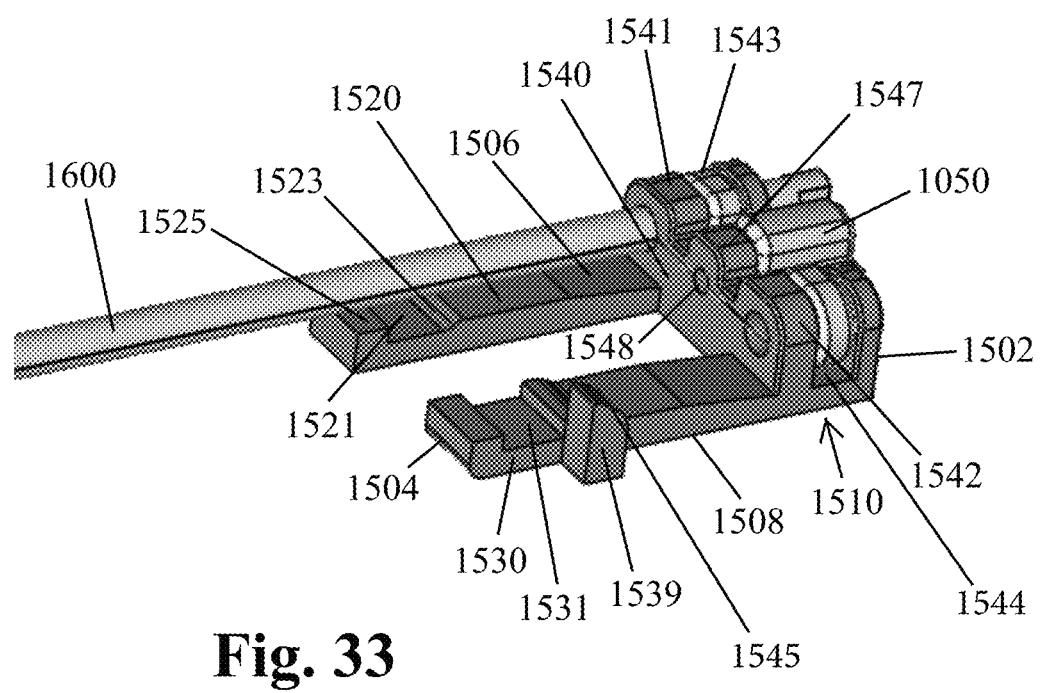
Figure 34:
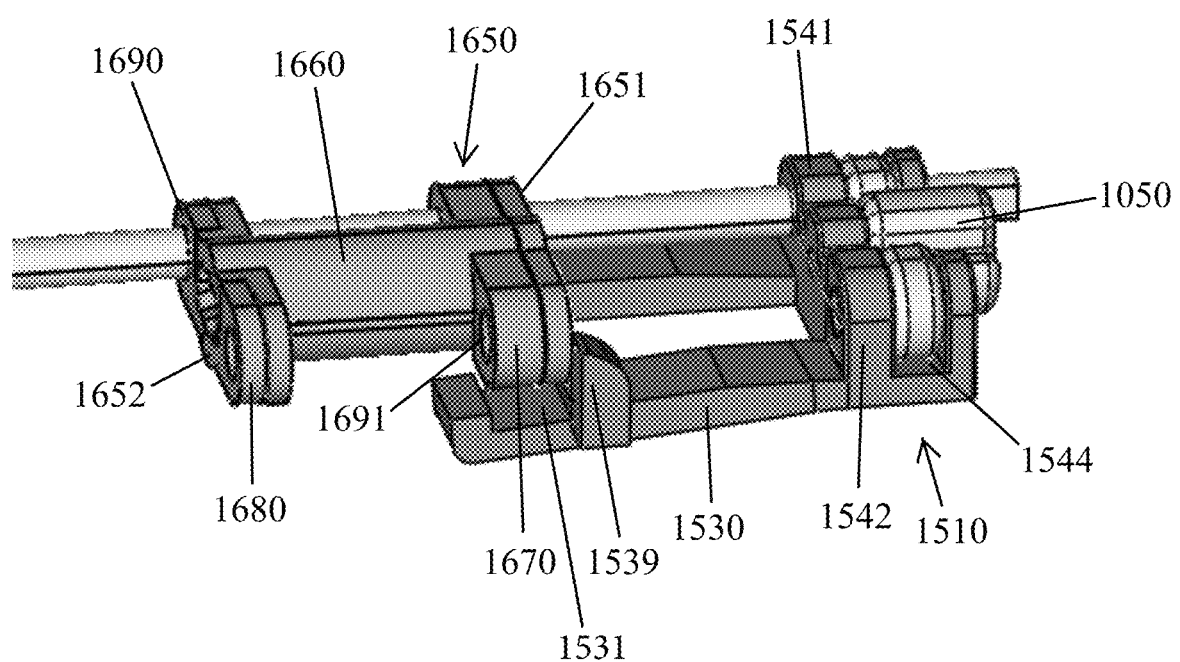

During a first cocking operation which facilitates uncoiling of the snare coil 1200 of the inner tube 1020 occurs when the lever/button 1810 pulls the curvilinear part 1650 backward while the movable base 1510 remains in place. The cocking mechanism can move the curvilinear part 1650 backward while the movable base 1510 remains steadfast because the curvilinear part 1650 has been mechanically uncoupled from the movable base 1510, and the moveable base 1510 is constrained from moving due to the interaction of the depressed leg 1520 with the stop 1339 (FIG. 31). The first cocking mechanism therefore translates the curvilinear part 1650 backward at which time the connection between the curvilinear part 1650 and movable base 1510 is reestablished.

More specifically, the button 1810 slides through the grooves and the button 1810 engages the curvilinear part 1650 and pushes the curvilinear part 1650 rearward toward the proximal end of the handle housing. The curvilinear part 1650 is thus moved back to the "uncoiled" position. As shown, the locking tab 1659 of the curvilinear part 1650 engages the raised protrusion (catch) 1335 of the flexible locking member 1330. This catch 1335 keeps the curvilinear part 1650 from returning to the fully fired position.

The second attribute of the button 1810 is a pair of swinging (pivoting) tabs 1830. The swinging tabs 1830 depend from the underside of the button 1810 and can swing (pivot) relative thereto. As shown, the top ends of each of the tabs 1830 receives a pin or axle that permits pivoting of the tabs 1830. As shown, each tab 1830 is received within one channel. The tabs 1830 are spaced apart from one another and are located at the second end 1816. The tabs 1830 are also biased (spring loaded) in that the tabs 1830 are spring loaded in the down position during a rest position of the button 1810.

Figure 41:
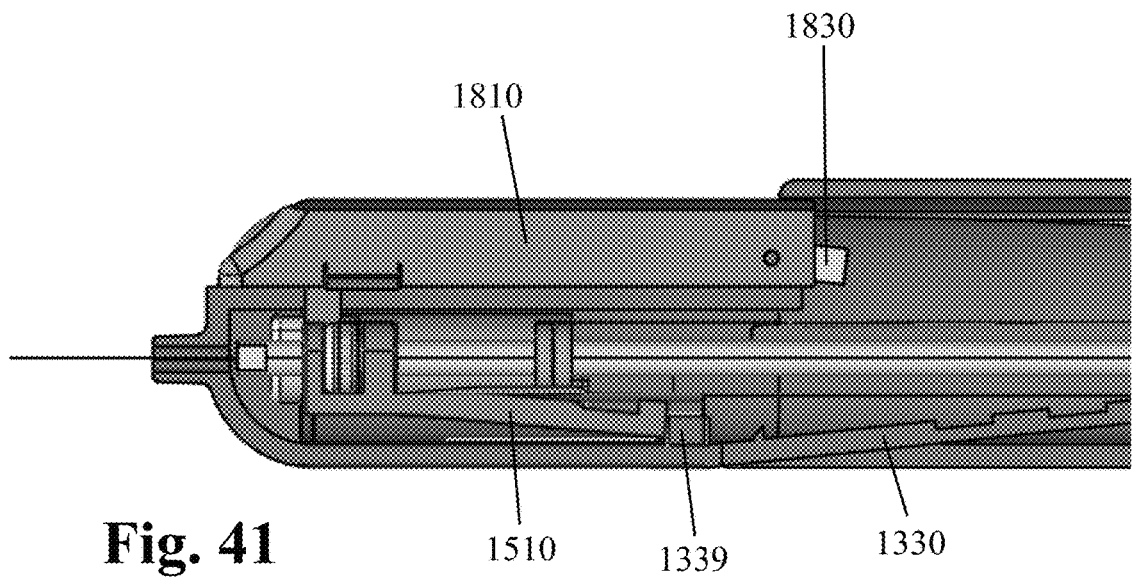
Figure 42:
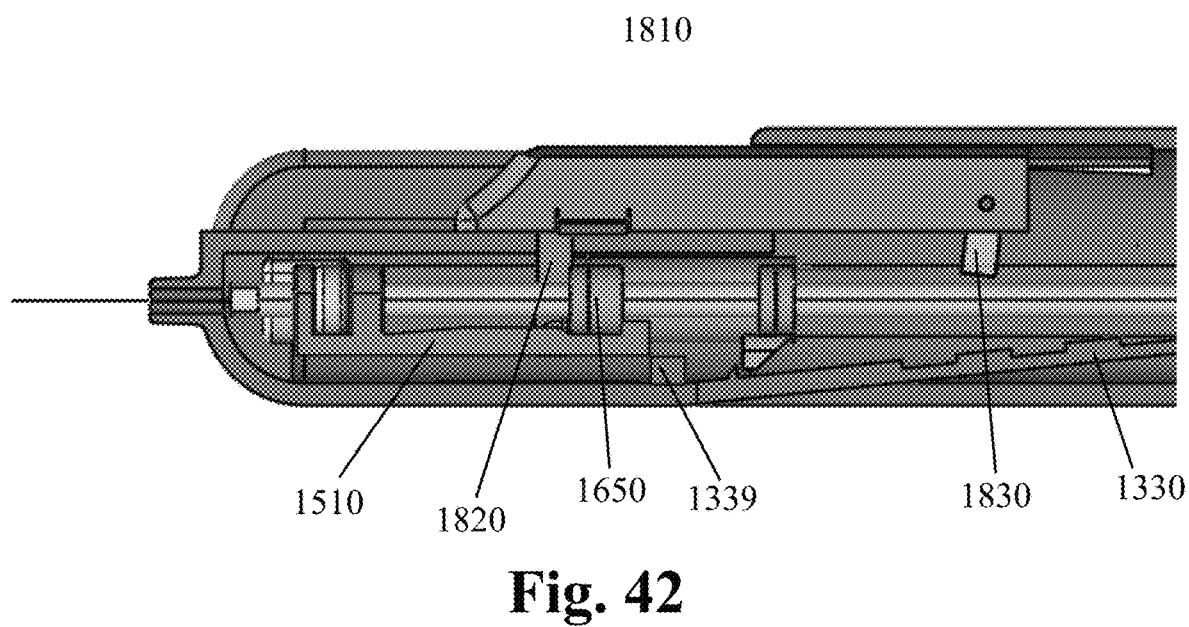

As shown in FIG. 41, the recess in the housing that contains the button 1810 is designed such that the swinging tabs 1830 are horizontal when the button 1810 is fully forward. The swinging tabs 1830 deploy (move downward) when the button 1810 is moved (e.g., slid within the housing). FIG. 41 shows the biopsy needle 1000 in the fully fired position and the button 1810 is in a fully forward position and the swinging tabs 1830 are in a raised position (i.e., are released up).

During the first cocking action (FIG. 42), the button 1810 is pushed inward and moves toward the proximal end of the handle and the two fixed tabs 1820 engage the curvilinear part 1650 as discussed here and drive the curvilinear part 1650 rearward (toward the proximal end of the housing). The swinging tabs 1830 swing down as the button 1810 moves rearward. However, during the first cocking operation, the swinging tabs 1830 do not engage any part and simply, as shown, depend down from the body of the button 1810.

As shown, in the first cocked position, the curvilinear part 1650 engages and is held by the flexible locking member (cantilevered structure) 1330.

Figure 43:
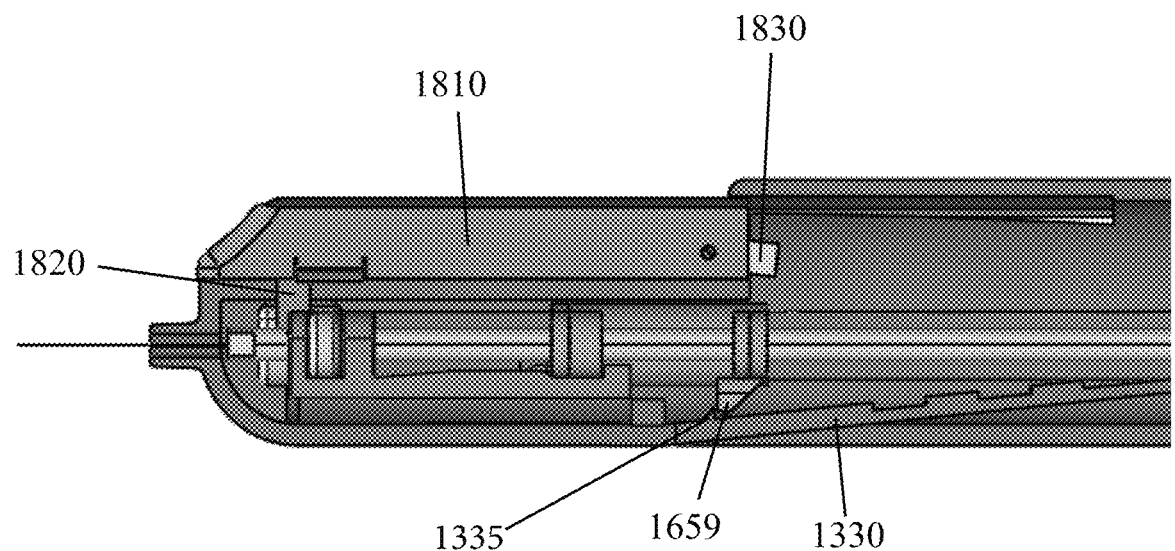

As shown in FIG. 43, the button 1310 is released and moves forward (due to the action of a biasing member or the like). As the button 1310 moves forward, the spring-loaded swinging tabs 1830 swing up when the swinging tabs 1830 such as by contact with the curvilinear part 1650 and the recess formed in the handle body forces them up into the retracted position.

Second Cocked Position

Once the connection is reestablished by the curvilinear part 1650 locking together with the movable base 1510 via the end portions of the legs 1520, 1530, a second cocking procedure is initiated where the cocking lever (button 1810) again connects to the curvilinear part 1650 pulling it backward.

Figure 44:
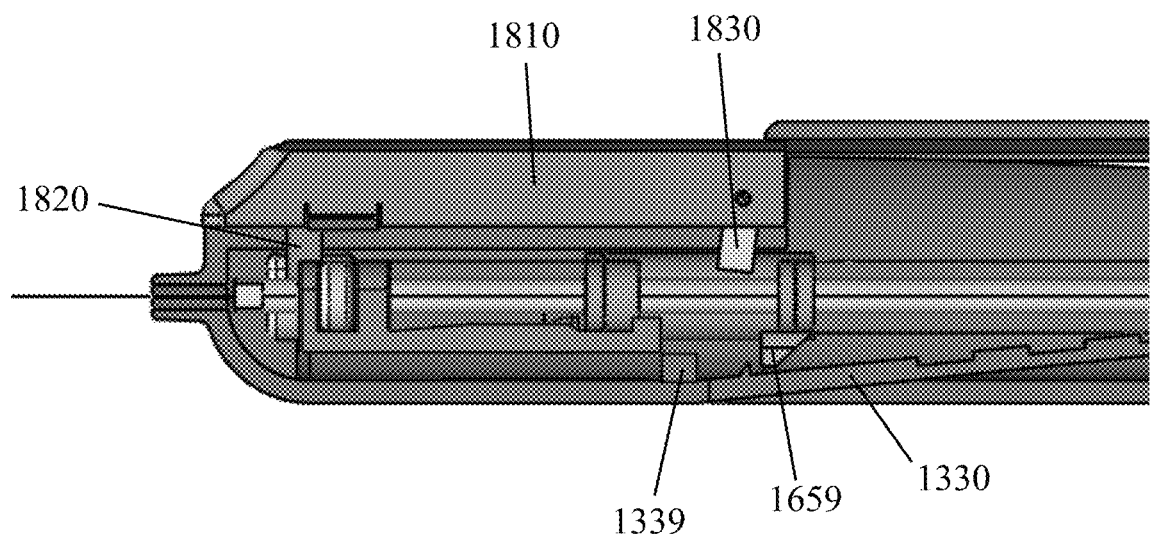
Figure 45:
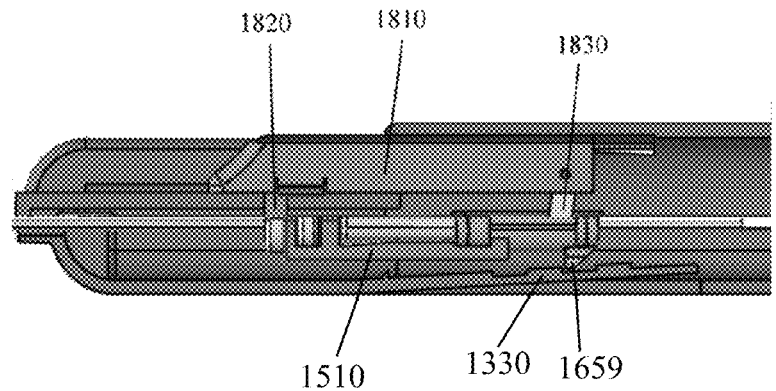

As shown in FIGS. 44 and 45, as the button 1810 is pushed back (rearward) as part of a second cocking operation, the swinging tabs 1830 swing downward (due to the biasing member thereof) and now engage the curvilinear part 1650 distally. With the swinging tabs 1830 engage with the curvilinear part 1650, the continued movement of the button 1810 causes the curvilinear part 1650 to be also moved. Since the connection between the curvilinear part 1650 and the movable part 1510 has been reestablished, the rearward movement of curvilinear part 1650 causes the rearward movement of the sled (movable base 1510) also and since the needle assembly is coupled to the sled, the needle assembly is also retracted relative to the stylet 1001 (which remains in the same position) allowing the specimen to be pushed out the front of the needle tip.

Thus, as the button 1810 is moved rearward, the curvilinear part 1650 is retracted within the handle housing. At the end of the second cocking operation, the curvilinear part 1650 then engages the flexible locking member (cantilevered structure) 1330 and the springs 1700, 1710, 1720 are compressed and store energy.

Figure 46:
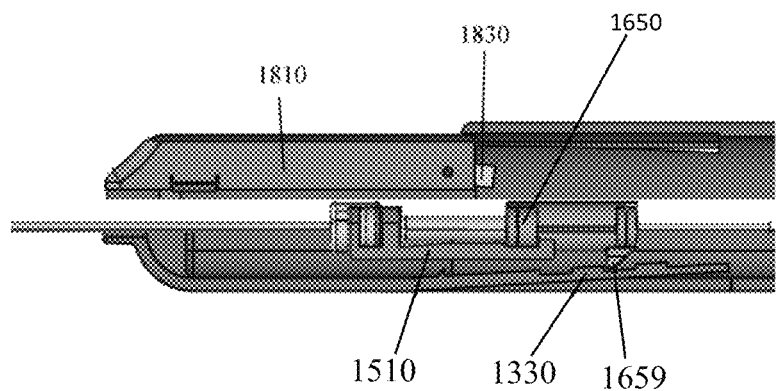

As shown in FIG. 46, the button 1810 is then released and is biased back to the forward position and as the button 1810 moves forward, the spring-loaded swinging tabs 1830 contact and "bounce" over the curvilinear part 1650 and back into the recess of the handle body so that they do not interfere with the subsequent firing of the needle.

Notably, the figures and examples above are not meant to limit the scope of the present invention to a single embodiment, as other embodiments are possible by way of interchange of some or all of the described or illustrated elements. Moreover, where certain elements of the present invention can be partially or fully implemented using known components, only those portions of such known components that are necessary for an understanding of the present invention are described, and detailed descriptions of other portions of such known components are omitted so as not to obscure the invention. In the present specification, an embodiment showing a singular component should not necessarily be limited to other embodiments including a plurality of the same component, and vice-versa, unless explicitly stated otherwise herein. Moreover, applicants do not intend for any term in the specification or claims to be ascribed an uncommon or special meaning unless explicitly set forth as such. Further, the present invention encompasses present and future known equivalents to the known components referred to herein by way of illustration.

The foregoing description of the specific embodiments will so fully reveal the general nature of the invention that others can, by applying knowledge within the skill of the relevant art(s) (including the contents of the documents cited and incorporated by reference herein), readily modify and/or adapt for various applications such specific embodiments, without undue experimentation, without departing from the general concept of the present invention. Such adaptations and modifications are therefore intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one skilled in the relevant art(s).

While various embodiments of the present invention have been described above, it should be understood that they have been presented by way of example, and not limitation. It would be apparent to one skilled in the relevant art(s) that various changes in form and detail could be made therein without departing from the spirit and scope of the invention. Thus, the present invention should not be limited by any of the above-described exemplary embodiments, but should be defined only in accordance with the following claims and their equivalents.

What is claimed is:

1. A biopsy needle for collecting a tissue specimen comprising:
a handle housing;
an outer cannula that is at least partially received within the handle housing;
an inner tube received within the outer cannula and configured to receive a stylet, wherein the outer cannula and inner tube extend distally beyond a distal end of the handle housing;
a snare coil attached between the inner tube and the outer cannula;
a movable base disposed within the handle housing, wherein the outer cannula is fixedly coupled to a needle holder that is fixedly coupled to and carried by a first end of the movable base, the movable base being axially movable within the handle housing, wherein the movable base includes a first deflectable leg, a second deflectable leg that is parallel to and spaced apart from the first deflectable leg, the first deflectable leg including a first notch that is defined by a straight distal wall and a proximal wall that comprises an angled cam surface, the second deflectable leg including a second notch;
an inner driven structure that is coupled to the inner tube and is detachably held within the first and second notches of the movable base and is configured to move axially within the housing with the movable base and further is configured to move axially across a surface of the movable base when the movable base is stationary and when the inner driven structure is detached from the movable base, wherein the inner driven structure is coupled to the inner tube is such that the axial driving of the inner driven structure imparts rotation to the inner tube relative to the outer cannula;
a first biasing mechanism configured to apply a biasing force to the inner driven structure for driving the inner driven structure and the movable base in a distal direction when the first biasing mechanism releases stored energy;
wherein in a first stage of operation, the inner driven structure is coupled to the movable base and the first biasing mechanism releases the stored energy to drive the coupled inner driven structure and movable base in the distal direction and at an end of the first stage of operation, the inner driven structure disengages from the movable base and the inner driven structure travels axially along the movable base in the distal direction to cause rotation of the inner tube relative to the outer cannula, thereby causing activation of the snare coil as part of a second stage of operation;
wherein the first and second deflectable legs deflect independent from one another, wherein the second deflectable leg is configured such that at the end of the first stage of operation, a cam surface of a side tab along an outer side of the second deflectable leg contacts a tab of the housing to cause downward deflection of the second deflectable leg.

2. The needle of claim 1, wherein a proximal end of the inner tube is disposed within a hollow interior of the inner driven structure.

3. The needle of claim 1, wherein the snare coil is located at a distal section of the inner tube with a distal end of the snare coil being attached to the outer cannula.

4. The needle of claim 1, wherein the inner driven structure comprises a curvilinear tube that includes a hollow base portion that includes at least one helical shaped groove formed therein, the inner tube including at least one protrusion extending outwardly from an outer surface thereof and being received within the at least one helical shaped groove.

5. The needle of claim 4, wherein the helical shaped groove passes completely through a side wall of the curvilinear tube.

6. The needle of claim 1, further including an elongated first guide and an elongated second guide spaced from the first guide and being parallel thereto, wherein each of the movable base and the inner driven structure is configured to travel axially along the first guide and the second guide.

7. The needle of claim 6, wherein each of the movable base, the needle holder, and the inner driven structure includes one or more enclosed circular openings that receive the first guide and the second guide to permit axial travel of the movable base, the needle holder and the inner driven structure along the first and second guides.

8. The needle of claim 1, wherein the inner driven structure is received within a pair of recesses formed along two legs of the movable base to detachably couple the inner driven structure to the movable base during the first stage of operation.

9. The needle of claim 6, wherein the movable base includes a base portion that extends between the first deflectable leg and the second deflectable leg, the base portion including a pair of enclosed circular openings that receive the first guide and the second guide, wherein the first and second deflectable legs define distal ends of the movable base.

10. The needle of claim 9, wherein the inner driven structure comprises a curvilinear tube and wherein in the first stage of operation, the curvilinear tube is attached to the movable base and wherein in the second stage of operation, the curvilinear tube disengages from the movable base and the curvilinear tube is configured to ride along the first and second deflectable legs.

11. The needle of claim 9, wherein the second stage of operation initiates when the second deflectable leg of the movable base deflects and the first deflectable leg includes a cam surface that defines one end of a first recess formed in the first deflectable leg that receives the inner driven structure in the first stage of operation, the cam surface permitting the inner driven structure to ride out of the recess and become disengaged from the movable base, whereby the first biasing mechanism drives the inner driven structure axially along the movable base in a distal direction.

12. The needle of claim 11, wherein the second deflectable leg engages the housing to keep the movable base and outer cannula and the inner tube from sliding in the proximal direction.

13. The needle of claim 1, wherein the first biasing mechanism comprises a pair of springs that seat against the inner driven structure.

14. The needle of claim 6, wherein the first guide and the second guide comprise rods and the first biasing mechanism comprises a pair of coil springs, with the first guide passing through a center of one spring and the second guide passing through a center of the other spring.

15. The needle of claim 1, further including a first actuator that selectively engages a flexible locking member that is coupled to the handle housing, the inner driven structure including a catch that selectively engages a recess formed in the flexible locking member to detachably couple the inner driven structure to the flexible locking member, whereby actuation of the first actuator causes deflection of the flexible locking member and release of the inner drive structure relative to the flexible locking member resulting in axial movement of the inner driven structure as part of the first stage of operation.

16. The needle of claim 1, further including a cocking mechanism to repositionally cock the movable base after the second stage of operation is completed.

17. The needle of claim 16, wherein the cocking mechanism is configured to act in two stages namely a first cocking stage in which the inner driven structure is moved axially in a proximal direction to an uncoiled position in which the snare is uncoiled and a second cocking stage in which the inner drive structure is moved to a fully activated position and is ready to undergo the first stage of operation.

18. The needle of claim 17, wherein the cocking mechanism includes a cocking actuator that moves axially along the handle housing and includes a pair of fixed legs protruding outwardly from the cocking actuator, the movable base including slots that permit axial passage of the pair of legs without engagement with the movable base as the cocking actuator moves in a proximal direction until the pair of legs engage the inner driven structure and drive the inner driven structure to the uncoiled position.

19. The needle of claim 18, wherein in the first cocked position, a locking tab of the inner driven structure engages a catch that is part of a flexible locking member that is coupled to the handle housing, thereby preventing the inner driven structure, which is under a biasing force in a distal direction due to the first biasing mechanism, from returning to a fully fired distal position.

20. The needle of claim 1, wherein the movable base includes a base portion that extends between the first deflectable leg and the second deflectable leg, the base portion including a pair of openings that receive an elongated first guide and an elongated second guide that permit axial travel of the movable base over the first and second guides, the second deflectable leg including a side tab located along and protruding outwardly from an outer edge of the second deflectable leg, the side tab including a cam surface that is configured to cause downward deflection of the second deflectable leg when the side tab contacts a structure located internally within the handle housing.

21. The needle of claim 20, further including a second biasing mechanism configured to apply a biasing force to the inner driven structure for driving the inner driven structure and the movable base in the distal direction when the second biasing mechanism releases stored energy, the first biasing mechanism being a first spring that surrounds the elongated first guide and the second biasing mechanism being a second spring that surrounds the elongated second guide.

22. The needle of claim 1, further including a cocking mechanism to repositionally cock the movable base after the second stage of operation is completed, wherein the cocking mechanism includes a cocking actuator that moves axially along an outer surface of the handle housing and includes a pair of fixed legs protruding outwardly at a first end of the cocking actuator and a pair of pivotable legs protruding outwardly at a second end of the cocking actuator.

23. The needle of claim 1, wherein the inner driven structure comprises a curvilinear tube that includes a locking tab that protrudes downwardly therefrom, the handle housing including a flexible locking member located along a bottom of the handle housing, the flexible locking member including a plurality of spaced locking recesses each of which is configured to receive the locking tab to detachably attach the curvilinear tube to the flexible locking member.

24. The needle of claim 23, wherein the handle housing includes a top part and a bottom part, wherein the flexible locking member comprises a cantilevered structure formed integrally along a floor of the bottom part and wherein the flexible locking member includes a catch in the form of a projection extending upwardly, with the plurality of spaced locking recesses being located between the catch and a free end of the flexible locking member.

25. The needle of claim 1, further including a first actuator to which the stylet is attached by a pin that passes through an opening in the first actuator, the first actuator including a distal rail, the pin defining a pivot axis of the first actuator, the distal rail being disposed above a flexible locking member and the first actuator being configured such that pivoting of the first actuator is translated into the distal rail contacting and pressing the flexible locking member downward to a depressed state.

* * * * *